(12) United States Patent
Ito et al.

(10) Patent No.: US 10,596,120 B2
(45) Date of Patent: Mar. 24, 2020

(54) PHARMACEUTICAL COMPOSITIONS

(71) Applicant: Boehringer Ingelheim International GmbH, Ingelheim am Rhein (DE)

(72) Inventors: Masanori Ito, Mainz (DE); Kenji Egusa, Osaka (JP); Roman Messerschmid, Kobe (JP); Peter Schneider, Ulm-Einsingen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 15/906,414

(22) Filed: Feb. 27, 2018

(65) Prior Publication Data

US 2018/0185291 A1    Jul. 5, 2018

Related U.S. Application Data

(63) Continuation of application No. 15/140,865, filed on Apr. 28, 2016, now abandoned, which is a continuation of application No. 13/413,702, filed on Mar. 7, 2012, now abandoned.

(30) Foreign Application Priority Data

Mar. 7, 2011 (EP) ..................... 11157240
Mar. 15, 2011 (EP) ..................... 11158358

(51) Int. Cl.
| | | |
|---|---|---|
| A61K 9/00 | (2006.01) | |
| A61K 9/24 | (2006.01) | |
| A61K 9/20 | (2006.01) | |
| A61K 9/28 | (2006.01) | |
| A61K 31/155 | (2006.01) | |
| A61K 45/06 | (2006.01) | |
| A61K 31/7048 | (2006.01) | |
| A61K 31/522 | (2006.01) | |

(52) U.S. Cl.
CPC ............ *A61K 9/209* (2013.01); *A61K 9/0053* (2013.01); *A61K 9/2054* (2013.01); *A61K 9/2813* (2013.01); *A61K 9/2853* (2013.01); *A61K 9/2866* (2013.01); *A61K 31/155* (2013.01); *A61K 31/522* (2013.01); *A61K 31/7048* (2013.01); *A61K 45/06* (2013.01)

(58) Field of Classification Search
None
See application file for complete search history.

(56) References Cited

U.S. PATENT DOCUMENTS

| | | |
|---|---|---|
| 3,174,901 A | 3/1965 | Sterne |
| 3,884,906 A | 5/1975 | Van Der Meer et al. |
| 4,379,785 A | 4/1983 | Weyer et al. |
| 4,602,023 A | 7/1986 | Kiely et al. |
| 4,639,436 A | 1/1987 | Junge et al. |
| 4,786,023 A | 11/1988 | Harris et al. |
| 4,786,755 A | 11/1988 | Kiely et al. |
| 4,802,924 A * | 2/1989 | Woznicki ............. A23G 3/2092 424/479 |
| 5,807,580 A | 9/1998 | Luber |
| 6,303,661 B1 | 10/2001 | Demuth et al. |
| 6,348,090 B1 * | 2/2002 | Grillo ................... A61K 9/286 106/162.1 |
| 6,414,126 B1 | 7/2002 | Ellsworth et al. |
| 6,448,323 B1 | 9/2002 | Jordan et al. |
| 6,515,117 B2 | 2/2003 | Ellsworth et al. |
| 6,613,806 B1 | 9/2003 | Aven et al. |
| 6,627,611 B2 | 9/2003 | Tomiyama et al. |
| 6,774,112 B2 | 8/2004 | Gougoutas |
| 6,794,480 B2 | 9/2004 | Goto et al. |
| 6,890,898 B2 | 5/2005 | Bachovhin et al. |
| 6,936,590 B2 | 8/2005 | Washburn et al. |
| 6,972,283 B2 | 12/2005 | Fujikura et al. |
| 6,995,183 B2 | 2/2006 | Hamann et al. |
| 7,109,192 B2 | 9/2006 | Hauel et al. |
| 7,169,761 B2 | 1/2007 | Tomiyama et al. |
| 7,173,028 B2 | 2/2007 | Dahmann et al. |
| 7,202,350 B2 | 4/2007 | Imamura et al. |
| 7,371,732 B2 | 5/2008 | Eickelmann et al. |
| 7,375,087 B2 | 5/2008 | Teranishi et al. |
| 7,375,090 B2 | 5/2008 | Himmelsbach et al. |
| 7,375,213 B2 | 5/2008 | Deshpande et al. |
| 7,393,836 B2 | 7/2008 | Eckhardt et al. |
| 7,407,955 B2 | 8/2008 | Himmelsbach et al. |
| 7,417,032 B2 | 8/2008 | Eckhardt et al. |
| 7,419,959 B2 | 9/2008 | Eckhardt et al. |
| 7,482,337 B2 | 1/2009 | Himmelsbach et al. |
| 7,501,426 B2 | 3/2009 | Himmelsbach et al. |
| 7,541,341 B2 | 6/2009 | Fushimi et al. |
| 7,579,449 B2 | 8/2009 | Eckhardt et al. |
| 7,589,193 B2 | 9/2009 | Washburn et al. |
| 7,662,790 B2 | 2/2010 | Himmelsbach et al. |
| 7,674,486 B2 | 3/2010 | Bhaskaran et al. |
| 7,683,160 B2 | 3/2010 | Eckhardt et al. |
| 7,687,469 B2 | 3/2010 | Eckhardt et al. |
| 7,713,938 B2 | 5/2010 | Himmelsbach et al. |
| 7,723,309 B2 | 5/2010 | Himmelsbach et al. |
| 7,745,414 B2 | 6/2010 | Eckhardt et al. |
| 7,772,191 B2 | 8/2010 | Eckhardt et al. |
| 7,772,192 B2 | 8/2010 | Esko |
| 7,772,378 B2 | 8/2010 | Himmelsbach et al. |

(Continued)

FOREIGN PATENT DOCUMENTS

| | | |
|---|---|---|
| CA | 2382480 A1 | 3/2001 |
| CA | 2388818 A1 | 4/2001 |

(Continued)

OTHER PUBLICATIONS

US Department of Health and Human Services, FDA, Endocrinologic and Metabolic Drugs Advisory Committee; Notice of Meeting, Federal Register, vol. 76, No. 80, Apr. 26, 2011, 23324-23325.

(Continued)

*Primary Examiner* — Nannette Holloman
(74) *Attorney, Agent, or Firm* — Edouard G. Lebel

(57) ABSTRACT

The present invention relates to pharmaceutical compositions comprising fixed dose combinations of a DPP-4 inhibitor drug and/or a SGLT-2 inhibitor drug, and metformin XR, processes for the preparation thereof, and their use to treat certain diseases.

22 Claims, No Drawings

(56) References Cited

U.S. PATENT DOCUMENTS

| | | |
|---|---|---|
| 7,772,407 B2 | 8/2010 | Imamura et al. |
| 7,776,830 B2 | 8/2010 | Eckhardt et al. |
| 7,820,815 B2 | 10/2010 | Pfrengle et al. |
| 7,847,074 B2 | 12/2010 | Eckhardt et al. |
| 7,851,502 B2 | 12/2010 | Bindra et al. |
| 7,851,602 B2 | 12/2010 | Himmelsbach et al. |
| 7,858,587 B2 | 12/2010 | Eckhardt et al. |
| 7,879,806 B2 | 2/2011 | Himmelsbach et al. |
| 7,879,807 B2 | 2/2011 | Himmelsbach et al. |
| 8,039,441 B2 | 10/2011 | Himmelsbach et al. |
| 8,071,583 B2 | 12/2011 | Himmelsbach |
| 8,106,060 B2 | 1/2012 | Pfrengle et al. |
| 8,119,648 B2 | 2/2012 | Himmelsbach et al. |
| 8,178,541 B2 | 5/2012 | Himmelsbach et al. |
| 8,232,281 B2 | 7/2012 | Dugi et al. |
| 8,283,326 B2 | 10/2012 | Eckhardt et al. |
| 8,507,450 B2 | 8/2013 | Eckhardt et al. |
| 8,551,957 B2 | 10/2013 | Dugi et al. |
| 8,557,782 B2 | 10/2013 | Eckhardt et al. |
| 8,802,842 B2 | 8/2014 | Weber et al. |
| 9,155,705 B2 | 10/2015 | Friedl et al. |
| 9,555,001 B2 | 1/2017 | Ito et al. |
| 9,949,997 B2 | 4/2018 | Broedl et al. |
| 9,949,998 B2 | 4/2018 | Broedl et al. |
| 10,258,637 B2 | 4/2019 | Broedl et al. |
| 10,406,172 B2 | 9/2019 | Eickelmann et al. |
| 2001/0041674 A1 | 11/2001 | Tomiyama et al. |
| 2001/0044435 A1 | 11/2001 | Himmelsbach et al. |
| 2002/0137903 A1 | 9/2002 | Ellsworth et al. |
| 2002/0173509 A1 | 11/2002 | Himmelsbach et al. |
| 2002/0198205 A1 | 12/2002 | Himmelsbach et al. |
| 2003/0064935 A1 | 4/2003 | Gougoutas |
| 2003/0087843 A1 | 5/2003 | Washburn |
| 2003/0104053 A1 | 6/2003 | Gusler et al. |
| 2003/0105077 A1 | 6/2003 | Kanstrup et al. |
| 2003/0114390 A1 | 6/2003 | Washburn et al. |
| 2004/0037883 A1 | 2/2004 | Zhou et al. |
| 2004/0087587 A1 | 5/2004 | Himmelsbach et al. |
| 2004/0097510 A1 | 5/2004 | Himmelsbach et al. |
| 2004/0138148 A1 | 7/2004 | Fushimi et al. |
| 2004/0138439 A1 | 7/2004 | Deshpande et al. |
| 2004/0180925 A1 | 9/2004 | Matsuno et al. |
| 2005/0065098 A1 | 3/2005 | Fujikura et al. |
| 2005/0085680 A1 | 4/2005 | Auerbach et al. |
| 2005/0124555 A1 | 6/2005 | Tomiyama et al. |
| 2005/0130985 A1 | 6/2005 | Himmelsbach et al. |
| 2005/0187168 A1 | 8/2005 | Eickelmann et al. |
| 2005/0209166 A1 | 9/2005 | Eckhardt et al. |
| 2005/0233982 A1 | 10/2005 | Himmelsbach et al. |
| 2005/0234108 A1 | 10/2005 | Himmelsbach et al. |
| 2005/0256310 A1 | 11/2005 | Hulin et al. |
| 2006/0002998 A1 | 1/2006 | Trehan et al. |
| 2006/0009400 A1 | 1/2006 | Eckhardt et al. |
| 2006/0019948 A1 | 1/2006 | Eckhardt et al. |
| 2006/0025349 A1 | 2/2006 | Eckhardt et al. |
| 2006/0035841 A1 | 2/2006 | Eckhardt et al. |
| 2006/0063722 A1 | 3/2006 | Washburn et al. |
| 2006/0074031 A1 | 4/2006 | Eckhardt et al. |
| 2006/0079541 A1 | 4/2006 | Langkopf et al. |
| 2006/0142210 A1 | 6/2006 | Eckhardt et al. |
| 2006/0142310 A1 | 6/2006 | Pfrengle et al. |
| 2006/0154866 A1 | 7/2006 | Chu et al. |
| 2006/0189548 A1 | 8/2006 | Himmelsbach et al. |
| 2006/0205711 A1 | 9/2006 | Himmelsbach et al. |
| 2006/0210627 A1 | 9/2006 | Pfeffer et al. |
| 2006/0234953 A1 | 10/2006 | Himmelsbach et al. |
| 2006/0247226 A1 | 11/2006 | Himmelsbach et al. |
| 2006/0251728 A1 | 11/2006 | Himmelsbach et al. |
| 2006/0258749 A1 | 11/2006 | Eckhardt et al. |
| 2007/0004648 A1 | 1/2007 | Himmelsbach et al. |
| 2007/0027092 A1 | 2/2007 | Himmelsbach et al. |
| 2007/0027168 A1 | 2/2007 | Pfrengle et al. |
| 2007/0049537 A1 | 3/2007 | Eckhardt et al. |
| 2007/0054867 A1 | 3/2007 | Eckhardt et al. |
| 2007/0060530 A1 | 3/2007 | Christopher et al. |
| 2007/0072813 A1 | 3/2007 | Himmelsbach et al. |
| 2007/0073046 A1 | 3/2007 | Eckhardt et al. |
| 2007/0077296 A1 | 4/2007 | Folger et al. |
| 2007/0212411 A1 | 9/2007 | Fawzy |
| 2007/0249544 A1 | 10/2007 | Himmelsbach et al. |
| 2007/0259821 A1 | 11/2007 | Eckhardt et al. |
| 2007/0259900 A1 | 11/2007 | Sieger et al. |
| 2007/0264370 A1* | 11/2007 | Jeffers ............... A61K 36/232 424/773 |
| 2007/0281940 A1 | 12/2007 | Dugi et al. |
| 2007/0293690 A1 | 12/2007 | Tomiyama et al. |
| 2007/0299076 A1 | 12/2007 | Piotrowski et al. |
| 2008/0058379 A1 | 3/2008 | Eckhardt et al. |
| 2008/0107731 A1 | 5/2008 | Kohlrausch et al. |
| 2008/0108816 A1 | 5/2008 | Zutter |
| 2008/0193529 A1 | 8/2008 | Kowalski et al. |
| 2008/0207882 A1 | 8/2008 | Derdau et al. |
| 2008/0234367 A1 | 9/2008 | Washburn et al. |
| 2008/0249089 A1 | 10/2008 | Himmelsbach et al. |
| 2008/0255159 A1 | 10/2008 | Himmelsbach et al. |
| 2008/0287529 A1 | 11/2008 | Deshpande et al. |
| 2009/0023913 A1 | 1/2009 | Eckhardt et al. |
| 2009/0137801 A1 | 5/2009 | Himmelsbach et al. |
| 2009/0192314 A1 | 7/2009 | Pfrengle et al. |
| 2009/0318547 A1 | 12/2009 | Eckhardt et al. |
| 2009/0326215 A1 | 12/2009 | Eckhardt et al. |
| 2010/0069310 A1 | 3/2010 | Himmelsbach et al. |
| 2010/0074950 A1 | 3/2010 | Sesha |
| 2010/0081625 A1 | 4/2010 | Wienrich et al. |
| 2010/0092124 A1 | 4/2010 | Magnusson et al. |
| 2010/0093654 A1 | 4/2010 | Himmelsbach et al. |
| 2010/0099641 A1 | 4/2010 | Himmelsbach et al. |
| 2010/0173916 A1 | 7/2010 | Himmelsbach et al. |
| 2010/0179191 A1 | 7/2010 | Himmelsbach et al. |
| 2010/0204250 A1 | 8/2010 | Himmelsbach et al. |
| 2010/0209506 A1 | 8/2010 | Eisenreich |
| 2010/0210662 A1 | 8/2010 | Baroni et al. |
| 2010/0240879 A1 | 9/2010 | Eckhardt et al. |
| 2010/0249392 A1 | 9/2010 | Eckhardt et al. |
| 2010/0298243 A1* | 11/2010 | Manuchehri ........ A61K 31/341 514/23 |
| 2010/0317847 A1 | 12/2010 | Eckhardt et al. |
| 2010/0330177 A1 | 12/2010 | Pourkavoos |
| 2011/0014284 A1 | 1/2011 | Eisenreich et al. |
| 2011/0046076 A1 | 2/2011 | Eickelmann et al. |
| 2011/0046087 A1 | 2/2011 | Eickelmann et al. |
| 2011/0065731 A1 | 3/2011 | Dugi et al. |
| 2011/0092510 A1 | 4/2011 | Klein et al. |
| 2011/0098240 A1 | 4/2011 | Dugi et al. |
| 2011/0112069 A1 | 5/2011 | Himmelsbach et al. |
| 2011/0144083 A1 | 6/2011 | Himmelsbach et al. |
| 2011/0144095 A1 | 6/2011 | Himmelsbach et al. |
| 2011/0178033 A1 | 7/2011 | Eckhardt et al. |
| 2011/0190322 A1 | 8/2011 | Klein et al. |
| 2011/0195917 A1 | 8/2011 | Dugi et al. |
| 2011/0206766 A1 | 8/2011 | Friedl et al. |
| 2011/0236477 A1 | 9/2011 | Schneider et al. |
| 2011/0237526 A1 | 9/2011 | Weber et al. |
| 2011/0237532 A1 | 9/2011 | De Vries et al. |
| 2011/0237789 A1 | 9/2011 | Weber et al. |
| 2011/0263493 A1 | 10/2011 | Dugi et al. |
| 2011/0263617 A1 | 10/2011 | Mark et al. |
| 2011/0275561 A1 | 11/2011 | Graefe-Mody et al. |
| 2011/0301182 A1 | 12/2011 | Dugi |
| 2012/0003313 A1 | 1/2012 | Kohlrausch et al. |
| 2012/0035158 A1 | 2/2012 | Himmelsbach et al. |
| 2012/0040982 A1 | 2/2012 | Himmelsbach et al. |
| 2012/0041069 A1 | 2/2012 | Sesha |
| 2012/0071403 A1 | 3/2012 | Strumph et al. |
| 2012/0094894 A1 | 4/2012 | Graefe-Mody et al. |
| 2012/0107398 A1 | 5/2012 | Schneider et al. |
| 2012/0121530 A1 | 5/2012 | Klein et al. |
| 2012/0122776 A1 | 5/2012 | Graefe-Mody et al. |
| 2012/0129874 A1 | 5/2012 | Sieger et al. |
| 2012/0142712 A1 | 6/2012 | Pfrengle et al. |
| 2012/0165251 A1 | 6/2012 | Klein et al. |
| 2012/0196812 A1 | 8/2012 | Eickelmann et al. |
| 2012/0208831 A1 | 8/2012 | Himmelsbach et al. |
| 2012/0219622 A1 | 8/2012 | Kohlrausch et al. |

(56) References Cited

U.S. PATENT DOCUMENTS

| | | |
|---|---|---|
| 2012/0219623 A1 | 8/2012 | Meinicke |
| 2012/0283169 A1 | 11/2012 | Grempler et al. |
| 2012/0296080 A1 | 11/2012 | Eckhardt et al. |
| 2012/0296091 A1 | 11/2012 | Sieger et al. |
| 2013/0035281 A1 | 2/2013 | Klein et al. |
| 2013/0035298 A1 | 2/2013 | Broedl et al. |
| 2013/0064887 A1 | 3/2013 | Ito et al. |
| 2013/0096076 A1 | 4/2013 | Dugi et al. |
| 2013/0137646 A1 | 5/2013 | Weinrich et al. |
| 2013/0236543 A1 | 9/2013 | Ito et al. |
| 2013/0252908 A1 | 9/2013 | Mayoux et al. |
| 2014/0031301 A1 | 1/2014 | Eickelmann et al. |
| 2014/0038911 A1 | 2/2014 | Eickelmann et al. |
| 2014/0046046 A1 | 2/2014 | Eckhardt et al. |
| 2014/0087996 A1 | 3/2014 | Klein et al. |
| 2014/0088027 A1 | 3/2014 | Grempler et al. |
| 2014/0256624 A1 | 9/2014 | Grempler et al. |
| 2014/0303097 A1 | 10/2014 | Broedl et al. |
| 2014/0303098 A1 | 10/2014 | Broedl et al. |
| 2014/0315832 A1 | 10/2014 | Broedl et al. |
| 2016/0000816 A1 | 1/2016 | Broedl et al. |
| 2016/0235680 A1 | 8/2016 | Ito et al. |
| 2017/0020907 A1 | 1/2017 | Eickelmann et al. |
| 2017/0095424 A1 | 4/2017 | Ito et al. |
| 2017/0305952 A1 | 10/2017 | Klein et al. |
| 2018/0104249 A1 | 4/2018 | Eisenreich |
| 2018/0169126 A1 | 6/2018 | Broedl et al. |
| 2018/0177794 A1 | 6/2018 | Wienrich et al. |
| 2018/0185291 A1 | 7/2018 | Ito et al. |
| 2018/0193427 A1 | 7/2018 | Grempler et al. |
| 2018/0200278 A1 | 7/2018 | Broedl et al. |
| 2018/0289678 A1 | 10/2018 | Eisenreich et al. |
| 2018/0344647 A1 | 12/2018 | Boeck et al. |
| 2019/0038654 A1 | 2/2019 | Broedl et al. |

FOREIGN PATENT DOCUMENTS

| | | |
|---|---|---|
| CA | 2437240 A1 | 8/2002 |
| CA | 2435730 A1 | 9/2002 |
| CA | 2463989 A1 | 4/2003 |
| CA | 2494177 A1 | 2/2004 |
| CA | 2496249 A1 | 3/2004 |
| CA | 2505389 A1 | 5/2004 |
| CA | 2470365 A1 | 6/2004 |
| CA | 2508024 A1 | 6/2004 |
| CA | 2508226 A1 | 6/2004 |
| CA | 2508233 A1 | 6/2004 |
| CA | 2526145 A1 | 9/2004 |
| CA | 2539032 A1 | 3/2005 |
| CA | 2544480 A1 | 6/2005 |
| CA | 2548353 A1 | 7/2005 |
| CA | 2555050 A1 | 9/2005 |
| CA | 2557269 A1 | 9/2005 |
| CA | 2557320 A1 | 9/2005 |
| CA | 2557801 A1 | 10/2005 |
| CA | 2569915 A1 | 1/2006 |
| CA | 2572149 A1 | 1/2006 |
| CA | 2572819 A1 | 1/2006 |
| CA | 2573777 A1 | 2/2006 |
| CA | 2574451 A1 | 2/2006 |
| CA | 2576294 A1 | 3/2006 |
| CA | 2574500 A1 | 4/2006 |
| CA | 2586938 A1 | 5/2006 |
| CA | 2617090 A1 | 2/2007 |
| CA | 2649922 A1 | 11/2007 |
| CA | 2651019 A1 | 11/2007 |
| CA | 2651089 A1 | 11/2007 |
| CA | 2696579 A1 | 2/2009 |
| CA | 2720450 A1 | 10/2009 |
| CA | 2726244 A1 | 12/2009 |
| CA | 2732803 A1 | 2/2010 |
| CA | 2735562 A1 | 2/2010 |
| CA | 2736421 A1 | 3/2010 |
| CA | 2738367 A1 | 4/2010 |
| CA | 2745037 A1 | 7/2010 |
| CA | 2745039 A1 | 7/2010 |
| CA | 2750798 A1 | 8/2010 |
| CA | 2752437 A1 | 8/2010 |
| CA | 2776296 A1 | 4/2011 |
| CA | 2782179 A1 | 6/2011 |
| CN | 101234105 A | 8/2008 |
| DE | 2758025 A1 | 7/1979 |
| DE | 2951135 A1 | 6/1981 |
| DE | 102004044221 A1 | 3/2006 |
| EP | 0206567 A2 | 12/1986 |
| EP | 1224195 B | 7/2002 |
| EP | 1344780 A1 | 9/2003 |
| EP | 1354888 A1 | 10/2003 |
| EP | 1385856 A | 2/2004 |
| EP | 1406873 A2 | 4/2004 |
| EP | 1500403 A1 | 1/2005 |
| EP | 1523994 A1 | 4/2005 |
| EP | 1553094 A1 | 7/2005 |
| EP | 1564210 A1 | 8/2005 |
| EP | 1586571 A1 | 10/2005 |
| EP | 1609785 A1 | 12/2005 |
| EP | 1791852 A2 | 6/2007 |
| EP | 1852108 A1 | 11/2007 |
| EP | 1852439 A1 | 11/2007 |
| EP | 2143443 A1 | 1/2010 |
| EP | 2166007 A1 | 3/2010 |
| JP | 55007256 A | 1/1980 |
| JP | 56039056 A | 4/1981 |
| JP | 58164502 | 9/1983 |
| JP | 62030750 A | 2/1987 |
| JP | 11124392 A | 5/1999 |
| JP | 2001288178 A | 10/2001 |
| JP | 2003511458 A | 3/2003 |
| JP | 2004196788 A | 7/2004 |
| JP | 2004359630 | 12/2004 |
| JP | 2005002092 A | 1/2005 |
| JP | 2005060625 A | 3/2005 |
| KR | 20070111099 A | 11/2007 |
| WO | 9718814 A1 | 5/1997 |
| WO | 9831697 A1 | 7/1998 |
| WO | 0116147 A1 | 3/2001 |
| WO | 0127128 A1 | 4/2001 |
| WO | 200152825 A2 | 7/2001 |
| WO | 0174834 A1 | 10/2001 |
| WO | 200197808 A1 | 12/2001 |
| WO | 200202560 A2 | 1/2002 |
| WO | 2002053573 A1 | 7/2002 |
| WO | 2002064606 A1 | 8/2002 |
| WO | 2002068420 A1 | 9/2002 |
| WO | 2002083066 A2 | 10/2002 |
| WO | 2003004496 A1 | 1/2003 |
| WO | 2003020737 A1 | 3/2003 |
| WO | 2003024965 A2 | 3/2003 |
| WO | 2003031458 A1 | 4/2003 |
| WO | 2003032997 A1 | 4/2003 |
| WO | 2003035177 A2 | 5/2003 |
| WO | 2003037327 A1 | 5/2003 |
| WO | 2003057200 A2 | 7/2003 |
| WO | 2003078404 A1 | 9/2003 |
| WO | 2003099836 A1 | 12/2003 |
| WO | 2004007517 A1 | 1/2004 |
| WO | 2004013118 A1 | 2/2004 |
| WO | 2004018468 A2 | 3/2004 |
| WO | 2004041820 A1 | 5/2004 |
| WO | 2004046115 A1 | 6/2004 |
| WO | 2004050658 A1 | 6/2004 |
| WO | 2004052902 A1 | 6/2004 |
| WO | 2004052903 A1 | 6/2004 |
| WO | 2004063209 A2 | 7/2004 |
| WO | 2004065380 A1 | 8/2004 |
| WO | 2004076470 A2 | 9/2004 |
| WO | 2004080990 A1 | 9/2004 |
| WO | 2005000848 A1 | 1/2005 |
| WO | 2005011786 A1 | 2/2005 |
| WO | 2005012318 A2 | 2/2005 |
| WO | 2005012326 A1 | 2/2005 |
| WO | 2005021566 A2 | 3/2005 |
| WO | 2005049022 A2 | 6/2005 |
| WO | 2005051950 A1 | 6/2005 |

(56) References Cited

FOREIGN PATENT DOCUMENTS

| | | |
|---|---|---|
| WO | 2005063785 A2 | 7/2005 |
| WO | 2005067976 A2 | 7/2005 |
| WO | 2005085237 A1 | 9/2005 |
| WO | 2005085246 A1 | 9/2005 |
| WO | 2005085265 A1 | 9/2005 |
| WO | 2005092877 A1 | 10/2005 |
| WO | 2005116014 A1 | 12/2005 |
| WO | 2005117861 A1 | 12/2005 |
| WO | 2006002912 A1 | 1/2006 |
| WO | 2006005613 A1 | 1/2006 |
| WO | 2006006496 A1 | 1/2006 |
| WO | 2006008038 A1 | 1/2006 |
| WO | 2006010557 A1 | 2/2006 |
| WO | 2006011469 A1 | 2/2006 |
| WO | 2006018150 A1 | 2/2006 |
| WO | 2006029769 A1 | 3/2006 |
| WO | 2006034489 A2 | 3/2006 |
| WO | 2006037537 A2 | 4/2006 |
| WO | 2006040625 A1 | 4/2006 |
| WO | 2006047248 A1 | 5/2006 |
| WO | 2006048427 A1 | 5/2006 |
| WO | 2006064033 A2 | 6/2006 |
| WO | 2006072334 A2 | 7/2006 |
| WO | 2006076231 A2 | 7/2006 |
| WO | 2006078593 A2 | 7/2006 |
| WO | 2006089872 A1 | 8/2006 |
| WO | 2006108842 A1 | 10/2006 |
| WO | 2006117359 A1 | 11/2006 |
| WO | 2006117360 A1 | 11/2006 |
| WO | 2006120208 A1 | 11/2006 |
| WO | 2006135693 A2 | 12/2006 |
| WO | 2007000445 A1 | 1/2007 |
| WO | 2007014886 A1 | 2/2007 |
| WO | 2007014894 A2 | 2/2007 |
| WO | 2007014895 A2 | 2/2007 |
| WO | 2007025943 A2 | 3/2007 |
| WO | 2007028814 A1 | 3/2007 |
| WO | 2007031548 A2 | 3/2007 |
| WO | 2007033350 A1 | 3/2007 |
| WO | 2007035665 A1 | 3/2007 |
| WO | 2007039417 A1 | 4/2007 |
| WO | 2007041053 A2 | 4/2007 |
| WO | 2007071738 A1 | 6/2007 |
| WO | 2007078726 A2 | 7/2007 |
| WO | 2007093610 A1 | 8/2007 |
| WO | 2007120702 A2 | 10/2007 |
| WO | 2007120936 A2 | 10/2007 |
| WO | 2007128721 A | 11/2007 |
| WO | 2007128724 A1 | 11/2007 |
| WO | 2007128749 A1 | 11/2007 |
| WO | 2007128761 A2 | 11/2007 |
| WO | 20070136151 A1 | 11/2007 |
| WO | 2007144175 A2 | 12/2007 |
| WO | 2007149797 A2 | 12/2007 |
| WO | 2008017670 A1 | 2/2008 |
| WO | 2008020011 A1 | 2/2008 |
| WO | 2008022267 A2 | 2/2008 |
| WO | 2008034859 A1 | 3/2008 |
| WO | 2008049923 A1 | 5/2008 |
| WO | 2008055870 A1 | 5/2008 |
| WO | 2008055940 A2 | 5/2008 |
| WO | 2008062273 A2 | 5/2008 |
| WO | 2008089892 A1 | 7/2008 |
| WO | 2008090210 A1 | 7/2008 |
| WO | 2008093878 A1 | 8/2008 |
| WO | 2008093882 A1 | 8/2008 |
| WO | 2008101938 A1 | 8/2008 |
| WO | 2008101939 A1 | 8/2008 |
| WO | 2008101943 A1 | 8/2008 |
| WO | 2008113000 A1 | 9/2008 |
| WO | 2008116179 A1 | 9/2008 |
| WO | 2008131149 A2 | 10/2008 |
| WO | 2009022007 A1 | 2/2009 |
| WO | 2009022008 A1 | 2/2009 |
| WO | 2009022009 A1 | 2/2009 |
| WO | 2009022010 A1 | 2/2009 |
| WO | 2009024542 A2 | 2/2009 |
| WO | 2009035969 A1 | 3/2009 |
| WO | 2009063072 A2 | 5/2009 |
| WO | 2009091082 A1 | 7/2009 |
| WO | 2009099734 A1 | 8/2009 |
| WO | 2009111200 A1 | 9/2009 |
| WO | 2009121945 A2 | 10/2009 |
| WO | 2009123992 A1 | 10/2009 |
| WO | 2009147125 A1 | 12/2009 |
| WO | 2010015664 A1 | 2/2010 |
| WO | 2010018217 A2 | 2/2010 |
| WO | 2010029089 A2 | 3/2010 |
| WO | 2010043688 A1 | 4/2010 |
| WO | 2010045656 A2 | 4/2010 |
| WO | 2010072776 A1 | 7/2010 |
| WO | 2010079197 A1 | 7/2010 |
| WO | 2010086411 A1 | 8/2010 |
| WO | 2010092123 A1 | 8/2010 |
| WO | 2010092124 A1 | 8/2010 |
| WO | 2010092125 A1 | 8/2010 |
| WO | 2010092126 A1 | 8/2010 |
| WO | 2010092163 A2 | 8/2010 |
| WO | 2010138535 A1 | 12/2010 |
| WO | 2010140111 A1 | 12/2010 |
| WO | 2010147768 A1 | 12/2010 |
| WO | 2011039107 A1 | 4/2011 |
| WO | 2011039108 A2 | 4/2011 |
| WO | 2011039337 A1 | 4/2011 |
| WO | 2011039367 A2 | 4/2011 |
| WO | 2011060290 A2 | 5/2011 |
| WO | WO-2011060256 A2 * | 5/2011 ............ A61K 9/209 |
| WO | 2011064352 A1 | 6/2011 |
| WO | 2011113947 A1 | 9/2011 |
| WO | 2011117295 A1 | 9/2011 |
| WO | 2011120923 A1 | 10/2011 |
| WO | 2011138380 A1 | 11/2011 |
| WO | 2011138421 A1 | 11/2011 |
| WO | 2011161161 A1 | 12/2011 |
| WO | 2011163206 A2 | 12/2011 |
| WO | 2012031124 A2 | 3/2012 |
| WO | 2012062698 A1 | 5/2012 |
| WO | 2012065993 A1 | 5/2012 |
| WO | 2012106303 A1 | 8/2012 |
| WO | 2012107476 A1 | 8/2012 |
| WO | 2012120040 A1 | 9/2012 |
| WO | 2013131967 A1 | 9/2013 |
| WO | 2013139777 A1 | 9/2013 |
| WO | 2014011926 A1 | 1/2014 |
| WO | 2016059219 A1 | 4/2016 |

OTHER PUBLICATIONS

US Department of Health and Human Services, FDA, "Guidance for Industry, Diabetes Mellitus—Evaluating Cardiovascular Risk in New Antidiabetic Therapies to Treat Type 2 Diabetes" Dec. 2008, 8 pages.
US Department of Health and Human Services, FDA, "Guidance for Industry, Pharmacokinetics in Patients with Impaired Renal Function—Study Design, Data Analysis, and Impact on Dosing and Labeling" May 1998, 19 pages.
US Department of Health and Human Services, FDA, Center for Drug Evaluation and Research "Application No: 204629Orig1s000 Summary Review (Jardiance)" 2014, 20 pages.
Valentine, Virginia "The Role of the Kidney and Sodium-Glucose Cotransporter-2 Inhibition in Diabetes Management" (2012) Clinical Diabetes, vol. 30, No. 4, 151-155.
Valk, Harold W. de "DPP-4 Inhibitors and Combined Treatment in Type 2 Diabetes: Re-evaluation of Clinical Success and Safety" (2007) The Review of Diabetic Studies, vol. 4, No. 3, 126-133.
Wallace, Debra J., et al; Cyclopropylboronic Acid: Synthesis and Suzuki Cross-Coupling Reactions; Tetrahedron Letters (2002) vol. 43 pp. 6987-6990; Pergamon Press.
Wang Y et al: "BI-1356. Dipeptidyl-peptidase IV inhibitor, antidiabetic agent" Drugs of the Future, Prous Science, ES, vol. 33, No. 6, Jun. 1, 2008, pp. 473-477.

(56) References Cited

OTHER PUBLICATIONS

Weber, Ann E. "Dipeptidyl Peptidase IV Inhibitors for the Treatment of Diabetes" (2004) J. Med. Chem., 47, 4135-4141.
Wettergren, Andre et al. "Truncated GLP-1 (Proglucagon 78-107-Amide) Inhibits Gastric and Pancreatic Functions in Man" (1993) Digestive Diseases and Sciences, vol. 38, No. 4, 665-673.
Wielert-Badt, Susanne et al. "Probing the Conformation of the Sugar Transport Inhibitor Phlorizin by 2D-NMR, Molecular Dynamics Studies, and Pharmacophore Analysis" (2000) J. Med. Chem., vol. 43, 1692-1698.
Wielert-Badt, Susanne et al. "Single Molecule Recognition of Protein Binding Epitopes in Brush Border Membranes by Force Microscopy" (2002) Biophysical Journal, vol. 82, 2767-2774.
Williams-Herman, D. et al., "Efficacy and safety of initial combination therapy with sitagliptin and metformin in patients with type 2 diabetes: a 54-week study". Current Medical Research and Opinion, Informa Healthcare, GB, vol. 25, No. 3, Jan. 2009, pp. 569-583.
Woo, Vincent C. "Dapagliflozin: where does it fit in the treatment of type 2 diabetes" (2009) Expert Opinion on Pharmacotherapy, 10(15): 2527-2535.
www.who.int/medicinedocs/index/assoc/s14141e/s14141e.pdf "Addendum 1 to The use of stems in the selection of International Nonproprietary names (INN) for pharmaceutical substances" World Health Organization Jun. 19, 2007, pp. 1-3, XP007906327.
Xue, Song., et al; Zinc-mediated Synthesis of Alpha-C-Glycosided from 1,2-Anhydroglycosides; Synletters (2003) vol. 6 pp. 870-872.
Yamada, Yuichiro et al. "Clinic: Careful Progress in the Field and new Therapeutic Methods" Medical Online, (2007) vol. 220, No. 13, pp. 1219-1221.
Zhang, L. et al "Dapagliflozin treatment in patients with different stages of type 2 diabetes mellitus: effects on glycaemic control and body weight" Diabetes, Obesity and Metabolism (2010) vol. 12, No. 6, pp. 510-515.
Zhang, Qiang et al. "Pharmaceuticals" Peking University Medical Press, Jan. 2005, first edition, partial English language translation, pp. 171-177.
Zimmermann, Grant R et al. "Multi-target therapeutics: when the whole is greater than the sum of the parts" (2007) Drug Discovery Today, vol. 12, 34-42.
Nauck, Michael A. et al. "Cardiovascular Actions and Clincial Outcomes with Glucagon-Like Peptide-1 Receptor Agonists and Dipeptidyl Peptidase-4 Inhibitors" Circulation (2017) vol. 136, 849-870.
Neamati, Ouri., et al;, "Depsides and Depsidones as Inhibiton of HIV-1 Integrase: Dimvery of Novel Inhibitors Through 3D Database Searclung", J. Med. Chem., 1997, vol. 40, pp. 942-951.
Nobre, Sabrina M., et al; Synthesis of Diarylmethane Derivatives from Pd-Catalyzed Cross-Coupling Reactions of Benzylic Halides with Arylboronic Acids; Tetrahedron Letters (2004) vol. 45 8225-8228.
Oku, Akira., et al; T-1095, An Inhibitor or renal Na+ -Glucose Cotransporters, May Provide a Novel Approach to Treating Diabetes; Diabetes (1999) vol. 48 pp. 1794-1800.
Pei, Z: "From the bench to the bedside: Dipeptidyl peptidase IV inhibitors, a new class of oral antihyperglycemic agents" Current Opinion in Drug Discovery and Development, Current Drugs, London, GB vol. 11, No. 4, Jul. 1, 2008 pp. 512-532.
Perner, Richard J., et al; 5,6,7-Trisubstituted 4-Aminopyrido[2,3-d]pyrimidines as Novel inhibitors of Adenosime Kinase; Journal of Medicinal Chemistry (2003) vol. 46 pp. 5249-5257.
Piya, Milan K. et al. "Emerging treatment options for type 2 diabetes" British Journal of Clinical Pharmacology, (2010) vol. 70, No. 5, pp. 631-644.
Plosker, Greg L. "Dapagliflozin: A Review of Its Use in Patients with Type 2 Diabetes" (2014) Drugs, 74, 2191-2209.
Pratley, Richard E. et al. "Inhibition of DPP-4: a new therapeutic approach for the treatment of type 2 diabetes" (2007) Current Medical Research and Opinion, vol. 23, No. 4, 919-931.

Printz, RIchard L. et al. "Tweaking the Glucose Sensor: Adjusting Glucokinase Activity with Activator Compounds" Endocrinology, (2005) vol. 146, No. 9, pp. 3693-3695.
Profit, Louise et al. "Vildagliptin: the evidence for its place in the treatment of type 2 diabetes mellitus" (2008) Core Evidence, 3(1), 13-30.
Pschyrembel et al. Clinical Dictionary, 257th Edition, Diabetes Mellitus, (1993) 320-321.
Rainier, Jon D. et al. "Aluminum- and Boron-Mediated C-Glycoside Synthesis from 1,2-Anhydroglycosides" Organic Letters, (2000) vol. 2, No. 17, pp. 2707-2709.
Randzio, Stanislaw L. et al. "Metastability and Instability of Organic Crystalline Substances" J. Phys. Chem. (2008) 112, pp. 1435-1444.
Redenti, Enrico et al. "Drug/Cyclodextrin/Hydroxy Acid Multicomponent Systems. Properties and Pharmaceutical Applications" Journal of Pharmaceutical Sciences, (2000) vol. 89, No. 1, pp. 1-8.
Revesz, Lasslo., et al; SAR of Benzoylpylpyridines and Benzophenones as p38 Alpha MAP Kinase Inhibitors with Oral Activity; Bioorganic & Medicinal Chemistry Letters (2004) vol. 14 pp. 3601-3605.
Riddle, Matthew "Combining Sulfonylureas and Other Oral Agents" (2000) The American Journal of Medicine, vol. 108 (6A), 15S-22S.
Riddle, Matthew C. "Oral Pharmacologic Management of Type 2 Diabetes" (1999) American Family Physician, 60(9), 2613-2620.
Robinson, J.A. "Chemical and Biochemical Aspects of Polyetherlonophore Antibiotic Biosynthesis" (1991) Progress in The Chemistry of Organic Natural Products, 1-81.
Rosenstock, et al., "Efficacy and tolerability of initial combination therapy with vildagliptin and pioglitazone compared with component montherapy in patients with type 2 diabetes". Diabetes, Obesity and Metabolism, Mar. 2007, vol. 9, No. 2, pp. 175-185.
Rosenstock, J. et al., "Alogliptin added to insulin therapy in patients with type 2 diabetes reduces HbA1c without causing weight gain or increased hypoglycaemia". Diabetes, Obesity and Metabolishm, Dec. 2009, vol. 11. No. 12, pp. 1145-1152.
Rosenstock, Julio et al. "Dipeptidyl peptidase-4 inhibitors and the management of type 2 diabetes mellitus" (2007) Current Opinion in Endocrinology, Diabetes & Obesity, vol. 14: 98—107.
Rudnic, Edward et al. "Oral Solid Dosage Forms" Remington's Pharmaceutical Sciences, 18th Ed, Gennaro, A.R. Ed, Macie Pub. Co. (1990) pp. 1633-1665.
Salgado Junior, et al. "Nonalcoholic fatty liver disease and obesity" Acti Cirugica Brasiliera (2006) vol. 21, Supp. 1, pp. 72-78.
Scheen, Andre J. "Pharmacokinetic considerations for the treatment of diabetes in patients with chronic kidney disease" (2013) Expert Opinion on Drug Metabolism and Toxicology, 9:5, 529-550.
Schernthaner, G et al. "How attractive is the combination of a sodium glucose co-transporter 2 inhibitor with a dipeptidyl peptidase 4 inhibitor in the treatment of type 2 diabetes" (2015) Diabetes, Obesity and Metabolism, 17, 313-615.
Scientific Discussion: "Eucreas. Scientific discussion". Online Oct. 2007, pp. 1-27, URL:http://www.emea.europa.eu/humandocs/PDFs/EPAR/eucreas/H-807-en6.pdf. see point 2. quality aspects pp. 2-4. (EMEA).
Scottish Medicines Consortium, Product Assessment "dapagliflozin 5mg and 10mg (Forxiga)" Sep. 2012, 14 pgs.
Sherwin, Robert S. et al. "The Prevention or Delay of Type 2 Diabetes" Diabetes Care, (2002) vol. 25, No. 4, pp. 742-749.
Shin-Yakuzaigaku Souron. Edited by Sadasuke Okano, published by Nankodo. 1987, vol. 3, pp. 255-256.
Silverman, et al. "Handbook of Grignard Reagents" Marcel Dekker (1996) p. 82.
Singhal, Dharmendra et al. "Drug polymorphism and dosage form design: a practical perspective" Advanced Drug Delivery Reviews, 56, (2004) pp. 335-347.
Softeland, Eirik et al. "Empagliflozin as Add-on Therapy in Patients with Type 2 Diabetes Inadequately Controlled With Linagliptin and Metformin: A 24-Week Randomized, Double-Blind, Parallel-Group Trial" (2016) Diabetes Care, DOI:10.2337/dc16-1347, pp. 1-9.
Sommer, Michael Bech., et al; displacement of Halogen of 2-Halogeno-Substituted Benzonitriles with Carbonions. Preparation of (2-Cyanoaryl)arylacetonitriles; Journal of Organic Chemistry (1990) vol. 55 pp. 1817-4821.

(56) References Cited

OTHER PUBLICATIONS

Stazi, Federica., et al; Statistical Experimental Design-Driven Discovery of room-Temperature Conditions for Palladium-Catalyzed Cyanation of Aryl Bromides; Tetrahedron Letters (2005) vol. 46 1815-1818; Elsevier Ltd.

Takebayashi, Kohzo et al. "Effect of Sodium Glucose Cotransporter 2 Inhibitors With Low SGLT2/SGLT1 Selectivity on Circulating Glucagon-Like Peptide 1 Levels in Type 2 Diabetes Mellitus" (2017) J Clin Med Res., vol. 9, (9) 745-753.

Tanaka, Chikako "Therapeutic Drugs for Metabolic Diseases, Chapter 2" (2002) New Yakurigaku (New Pharmacology) pp. 524-527.

Taskinen, M.-R. et al., "Safety and efficacy of linagliptin as add-on therapy to metformin in patients with type 2 diabetes: a randomized, double-blind, placebo-controlled study." Diabetes, Obesity and Metabolism, 2011, vol. 13, pp. 65-74.

The Merck Manual Diagnosis and Therapy; Seventeenth Edition; "13 / Disorders of Carbohyrate Metabolism" Merck Research Laboratories (1999) pp. 165-177.

Thomas, L., "Chronic treatment with the Dipeptidyl Peptidase-4 Inhibitor BI 1356[9R)-8-(3-Amino-piperidin-1-yl)-7-but-2-ynyl-3-methyl-1(4-methyl-quinazolin-2-ylmethyl)-3,7-dihydro-purine-2,6-dione] Increases Basal Glucagon-Like Peptide-1 and Improves Glycemic Control in Diabetic Rodent Models" The Journal of Pharmacology and Experimental Therapeutics, Feb. 2009, vol. 328, No. 2, pp. 556-563.

Thomas, Leo "Long-term treatment with empagliflozin, a novel, potent and selective SGLT-2 inhibitor, improves glycaemic control and features of metabolic syndrome in diabetic rats" (2012) Diabetes, Obesity and Metabolism, vol. 14, No. 1, 94-96.

Thomas, Leo et al. "(R)-8-(3-Amino-piperidin-1-yl)-7-but-2-ynyl-3-methyl-1-(4-methyl-quinazolin-2-ylmethyl)-3,7-dihydro-purine-2,6-dione (BI 1356), a Novel Xanthine-Based Dipeptidyl Peptidase 4 Inhibitor, Has a Superior Potency and Longer Duration of Action Compared with Other Dipeptidyl Peptidase-4 Inhibitors" Journal of Pharmacology and Experimental Therapeutics (2008) 325, pp. 175-182.

Threlfall, Terry "Structural and Thermodynamic Explanations of Ostwald's Rule" Organic Process Research & Development (2003) vol. 7, pp. 1017-1027.

Tinahones, Francisco J. et al. "Linagliptin as add-on to empagliflozin and metformin in patients with type 2 diabetes: Two 24-week randonmized double-blind, double-dummy parallel-group trials" (2017) Diabetes Obes Metab, 19(2): 266-274.

Torrance, Christopher J. et al. "Combinatorial chemoprevention of intestinal neoplasia" (2000) Nature Medicine, vol. 5, No. 8, 1024-1028.

Turner, Robert C. et al. "Glycemic Control with Diet, Sulfonylurea, Metformin or Insulin in Patients with Type 2 Diabetes Mellitus, Progressive Requirement for Multiple Therapies (UKPDS-49)" (1999) American Medical Association, vol. 281, No. 21, 8 pgs.

Tykwinski, Rik R; Evolution in the Palladium-Catalyzed Cross-Coupling of sp- and sp2-Hybridized Carbon Atoms; Angew Chemical International Edition (2003) vol. 42 pp. 1566-1568.

Ueta, Kiichiro., et al; Long-Term Treatment with the Na+ -Glucose Cotransporter Inhibitor T-1095 Causes Sustained Improvement in Hyperglycemia and Prevents Diabetic Neuropathy in Goto-Kakizaki Rats; Life Sciences (2005) vol. 76 pp. 2655-2668.

US Department of Health and Human Services, CDER, FDA, "Guideline for Submitting Supporting Documentation in Drug Applications for the Manufacture of Drug Substances" Feb. 1987, 48 pages.

International Search Report for PCT/EP2010/051736 dated May 7, 2010.

International Search Report for PCT/EP2012/053910 dated May 14, 2012.

International Search Report for PCT/EP2013/054524 dated May 6, 2013.

International Search Report PCT/EP2016/079465 filed on Dec. 1, 2016.

Inzucchi, Silvo E. "Oral Antihyperglycemic Therapy for Type 2 Diabetes" (2002) JAMA, vol. 287, No. 3, 360-372.

Isaji, Masayuki "Sodium-glucose cotransporter inhibitors for diabetes" Current Opinion in Investigational Drugs, (2007) vol. 8, No. 4, pp. 285-292.

Jabbour, S.A. et al. "Sodium glucose co-transporter 2 inhibitors: blocking renal tubular reabsorption of glucose to improve glycaemic control in patients with diabetes" (2008) Int J Clin Pract, 62, 8, 1279-1284.

Jagdmann Jr, G. Erik ; Synthesis of 5-(4-Substituted Benzyl)-2,4-Diaminoquinazolines as Inhibitors of Candida Albicans Dihydrofolate Reductase; Journal Heterocyclic Chemical (1995) vol. 32 pp. 1461-1465.

Johnson & Johnson "FDA Advisory Committee Recommends Approval of Canagliflozin for Treatment of Adults with Type 2 Diabetes" (2013) Press Release, 3 pgs.

Kadowaki, T et al. "PPAR gamma agonist and antagonist" Nihon Yakurigaku Zasshi (2001) vol. 118, No. 9, pp. 321-326. (English abstract).

Katsuno, Kenji et al. "Sergliflozin, a Novel Selective Inhibitor of Low-Affinity Sodium Glucose Cotransporter (SGLT2) Validates the Critical Role of SGLT2 in Renal Glucose Reabsorption and Modulates Plasma Glucose Level" The Journal of Pharmacology and Experimental Therapeutics (2007) vol. 320, No. 1, pp. 323-330.

Knochel, Paul et al. "Highly functionalized Organomagnesium Reagents Prepared through Halogen-Metal Exchange" Angew. Chem. INt. Ed. (2003) vol. 42, 4302-4320.

Koo, Ja Seo., et al; 2-Pyridyl Cyanate: A Useful Reagent for he Preparation of Nitriles; Synthetic Communications (1996) vol. 26 No. 20 pp. 3709-3713; Marcel Dekker, Inc.

Krasovskiy Arkady et al. "A LiCL-Mediated Br/Mg Exchange Reaction for the Preparation of Functionalized Aryl-and Heterarylmagnesium Compounds from Organic Bromides**" Angew. Chem. Int. Ed. (2004) vol. 43, pp. 3333-3336.

Kuribayashi, Takeshi., et al; Bis C-Glycosylated Diphenylmethanes for Stable Glycoepitope Mimetics; Syntletters (1999) vol. 6 pp. 737-740.

Kuribayashi, Takeshi., et al; c-Glycosylated Aryl tins: Versatile Building Blocks for Aryl C-Glycoside Glycomimetics; J. Carbohydrate Chemistry (1999) vol. 18, No. 4 pp. 371-382.

Kuribayashi, Takeshi., et al; C-Glycosylated Diphenylmethanes and Benzophenones: The Stille Coupling Reaction of C-Glycosylated Aryl tins with Benzyl Bromides and Acid Chlorides; J. Carbohydrate Chemistry (1999) vol. 18, No. 4 pp. 393-401.

Langle, Sandrine., et al; Selective Double Suzuki Cross-Coupling Reactions. Synthesis of Unsymmetrical Diaryl (or Heteroaryl) Methanes; Tetrahedron Letters (2003) vol. 44 pp. 9255-9258; Pergamon Press.

Langley, Alissa K. et al. "Dipeptidyl Peptidase IV Inhibitors and the Incretin System in Type 2 Diabetes Mellitus" (2007) Pharmacotherapy, vol. 27, 1164-1180.

Larsen, Mogens Lytken et al. "Effect of Long-Term Monitoring of Glycosylated Hemoglobin Levels in Insulin-Dependent Diabetes Mellitus" (1990) The New England Journal of Medicine, vol. 323, No. 15, 1021-1025.

Lebovitz, Harold E. "Insulin secretagogues: old and new" (1999) Diabetes Review, vol. 7, 139-153.

Lehmann, Ule et al. "Palladium-Catalyzed Cross-Coupling Reactions between Dihydropyranylindium Reagents and Aryl Halides, Synthesis of C-Aryl Glycals" Organic Letters, 2003, vol. 5, No. 14, pp. 2405-2408.

Levetan, Claresa "Oral antidiabetic agents in type 2 diabetes" (2007) Current Medical Research and Opinion, vol. 23, No. 4, 945-952.

Levey Andrew S. et al. "Definition and classification of chronic kidney disease: A position statement from Kidney Disease: Improving Global Outcomes (KDIGO)" (2005) Kidney International, vol. 67, 2089-2100.

Levien, T.L. et al, "New drugs in development for the treatment of diabetes", Diabetes Spectrum, American Diabetes Association, US, vol. 22, No. 2, Jan. 1, 2009, pp. 92-106.

Lewin Andrew et al "Initial Combination of Empagliflozin and Linagliptin in Subjects with Type 2 Diabetes" (2015) . Diabetes Care, vol. 38, 394-402.

(56) References Cited

OTHER PUBLICATIONS

Li, T et al. "Lack of Pharmacokinetic Interaction between Dapagliflozin and Pioglitazone in Healthy Subjects" Journal of Clinical Pharmacology, (2009) vol. 49, No. 9, p. 1093.
Li, Yazhou, et al. "Glucagon-like Peptide-1 Receptor Signaling Modulates b Cell Apoptosis" (2003) The Journal of Biological Chemistry, vol. 278, No. 1, 471-478.
Lieberman, Herbert A. et al. "Pharmaceutical Dosage Forms: Tablets, vol. 1" (1989) pp. 5-6.
Lipworth, Brian J. "Clinical pharmacology of b3-adrenoceptors" Br J Clin Pharmacol (1996) pp. 291-300.
Matsuyama, Tatsuo et al. "Glucagon-like peptide-1 (7-36 amide): a potent glucagonostatic and insulinotropic hormone" Diabetes Research and Clincial Practice (1988) 5, 281-284.
McHale, Mary "Grignard Reaction" Connexions module: m15245, (2007) pp. 1-18.
McKinney, James D. et al. "The Practice of Structure Activity Relationships (SAR) in Toxicology" (2000) Toxicological Sciences, vol. 56, 8-17.
McLaughlin, Mark, et al; Suzuki-Miyaura Cross-Coupling of Benzylic Phospahates with Arylboronic Acids; Organic Letters (2005) vol. 7 No. 22 pp. 4875-4878.
McMaster University, Chem2006 Lab Manual, 1997/98, Expt 1, Part B, pp. 1-9.
Meece, J. "When Oral Agents Fail: Optimizing Insulin Therapy in the Older Adult". Consultant Pharmacist, The Society, Arlington, VA US. vol. 24, No. Suppl B, Jun. 1, 2009, pp. 11-17.
Meng, Wei et al "Discovery of Dapagliflozin: A Potent, Selective Renal Sodium-Dependent Glucose Cotransporter 2 (SGLT2) Inhibitor for the Treatment of Type 2 Diabetes" J. Med. Chem. (2008) vol. 51, pp. 1145-1149.
Merck Manual of Diagnosis and Therapy, 17th Edition, (1999) Ch 13 / Disorders of Carohydrate Metabolism, Diabetes Mellitus. pp. 165-177.
Merck Manual Online Edition, "Diabetes Mellitus" http://www.merckmanuals.com/professional/endocrine_and_metabolic_disorders/diabetes_mellitus_and_disorders of carbohyrate_metabolism/diabetes_mellitus_dm.html#v987998. last revision Jun. 2008 by Preeti Kishore M.D.
Merck: "Initial Therapy with Janumet (sitagliptin/metformin) provided significantly greater blood sugar lowering compared to metformin alone in patients with type 2 diabetes". Webwire.com, Jun. 8, 2009, pp. 1-4. http://www.webwire.com/ViewPressRel.asp?aId=96695.
Merriam-Webster's Collegiate Dictionary, published 1998 by Merriam-Webster INC. "prevent".
Meyer, Timothy W. "Tubular injury in glomerular disease" (2003) Kidney International, vol. 63, pp. 774-787.
Mojsov, Svetlana "Insulinotropin: Glucagon-like Peptide I (7-37) Co-encoded in the Glucagon Gene Is a Potent Stimulator of Insulin Release in the Perfused Rat Pancreas" J. Clin. Invest. (1987) vol. 79, 616-619.
Mooradian, Arsharg D. et al. "Narrative Review: A Rational Approach to Starting Insulin Therapy" (2006) Annals of Internal Medicine, vol. 145, pp. 125-134.
Munir, Kashif et al. "Differential pharmacology and clinical utility of empagliflozin in type 2 diabetes" (2016) Clinical Pharmacology: Advances and Applications, vol. 8, 19-34.
Nathan, D.M. et al. "Medical management of hyperglycaemia in type 2 diabetes mellitus: a consensus algorithm for the initiation and adjustment of therapy" Diabetologia (2009) 52, 17-30.
Nathan, David M. et al. "Management of Hyperglycemia in Type 2 Diabetes: A Consensus Algorithm for the Initiation and Adjustment of Therapy" (2006) Diabetes Care, vol. 29, No. 8, 1963-1972.
Nathan, David M. et al. "Medical Management of Hyperglycemia in Type 2 Diabetes: A Consensus Algorithm for the Initiation and Adjustment of Therapy" (2009) vol. 32, No. 1, pp. 193-203.
National Institute for Health Research, Horizon Scanning Centre, "Empagliflozin for type 2 diabetes mellitus" Apr. 2012, 10 pgs.
National Kidney Foundation, "Clinical Practice Guidelines, for Chronic Kidney Disease: Evaluation, Classification and Stratification" (2002) 356 pgs.
Eckhardt, M. et al., "8-(3-(R)-Aminopiperidin-1-yl)-7-but-2-ynyl-3-methyl-1-(4-methyl-quinazolin-2-ylmethyl)-3,7-dihydropuring-2,6-dione (BI1356), a Highly Potent, Selective, Long-Acting, and Orally Bioavailable DPP-4 Inhibitor for the Treatment of Type 2 Diabetes" J. Med Chem (2007) vol. 50, pp. 6450-6453.
European Medicines Agency, Science Medicines Health, "Assessment Report Forxiga dapagliflozin" (2012) 170 pgs.
FDA Formal Comments on "Draft Guidance for Industry on Powder Blends and Finished Dosage Units—Stratified In-Process Dosage Unit Sampling and Assessment" Jan. 21, 2004, 54 pgs.
Ferrannini, Ele et al. "Metabolic response to sodium-glucose cotransporter 2 inhibition in type 2 diabetic patients" (2014) The Journal of Clinical Investigation vol. 124, No. 2, 499-508 and article amendment, p. 1868.
Ferrannini, Ele et al. "SGLT2 inhibition in diabetes mellitus: rationale and clinical prospects" (2012) Nat. Rev. Endocrinol. vol. 8, 495-502.
Fiese, Eugene F et al. "Preformulation" (1987) The Theory and Practice of Industrial Pharmacy, 28 pgs.
Final Office Action dated Dec. 10, 2012, U.S. Appl. No. 12/703,988, filed Feb. 11, 2010. Inventor: Peter Eickelmann.
Fuerstner, Alois., et al; Practical Method for the Rhodium-Catalyzed Addition of Aryl- and Alkenylboronic Acids to Aldehydes; Advanced Synthesis and Catalysis (2001) vol. 343 No. 4 pp. 343-350.
Fujimori, Yoshikazu et al. "Remogliflozin Etabonate in a Novel Category of Selective Low-Affinity Sodium Glucose Cotransporter (SGLT2) Inhibitors, Exhibits Antidiabetic Efficacy in Rodent Models" (2008) Journal of Pharmacology and Experimental Therapeutics vol. 327 No. 1, pp. 268-276.
Gallwitz, B. "Sitagliptin with Metformin: Profile of a Combination for the Treatment of Type 2 Diabetes". Drugs of Today, Oct. 2007, 43(10), pp. 681-689.
Gallwitz, Baptist "Saxagliptin, a dipeptidyl peptidase IV inhibitor for the treatment of type 2 diabetes", IDrugs (2008) 11(12), pp. 906-917.
Garber, A.J. et al. "Vildagliptin in combination with pioglitazone improves glycaemic control in patients with type 2 diabetes failing thiazolidinedione monotherapy: a randomized, placebo-controlled study" (2007) Diabetes, Obesity and Metabolism, 9, 166-174.
Gennaro, Alfonso R. "Remington: The Science and Practice of Pharmacy" Twentieth Edition (2000) 4 pgs.
Gerich, John E. "Matching Treatment to Pathophysiology in Type 2 Diabetes" (2001) Clinical Therapeutics, vol. 23, No. 5, 646-659.
Ghassemi et al. "Synthesis and properties of new sulfonated poly(p-phenylene) derivatives for proton exchange membranes" Polymer (2004) pp. 5847-5854.
Ghosh, Raktim Kumar et al. "SGLT2 Inhibitors: A New Emerging Therapeutic Class in the Treatment of Type 2 Diabetes Mellitus" (2012) Journal of Clinical Pharmacology, 52, 457-463.
Golay A. et al. "Link Between Obesity and Type 2 Diabetes" (2005) Best Practice & Research Clinical Endocrinology & Metabolism, vol. 19, No. 4, 649-663.
Goldstein, Barry J. et al. "Effect of Initial Combination Therapy with Sitagliptin, a Dipeptidyl Peptidase-4 Inhibitor and Metformin on Glycemic Control in Patients with Type 2 Diabetes" (2007) Diabetes Care, vol. 30, No. 8, 1979-1987.
Graefe-Mody et al., "The novel DPP-4 inhibitor . . ." Diabetes, (online) 2008, XP002561421 http://professional.diabetes.org/content/posters/2008/p553-p.pdf.
Graefe-Mody, E.U., et al., "Evaluation of the potential for steady-state pharmacokinectic and pharmacodynamic interactions between the DPP-4 inhibitor linagliptin and metformin in healthy subjects". Current Medical Research and Opinion, Informa Healthcare, GB, vol. 25. No. 8, Aug. 1, 2009, pp. 1963-1972.
Greco, Gary T. et al. "Segregation of Active Constituents from Tablet Formulations During Grinding: Theoretical Considerations" Drug Development and Industrial Pharmacy, (1982) 8(4), pp. 565-578.

(56) References Cited

OTHER PUBLICATIONS

Green, Brian D. et al "Dipeptidyl peptidase IV (DPP IV) inhibitors: a newly emerging drug class for the treatment of type 2 diabetes" (2006) Diabetes and Vascular Disease Research, 159-165.
Guillory, J. Keith "Generation of Polymorphs, Hydrates, Solvates and Amorphous Solids" Polymorphism in Pharmaceutical Solids (1999) 46 pgs.
Gupta, Rajesh et al. "Emerging Drug Candidates of Dipeptidyl Peptidase IV (DPP IV) Inhibitor Class for the Treatment of Type 2 Diabetes" (2009) Current Drug Targets, vol. 10, No. 1, 71-87.
Gwaltney, S. "Medicinal Chemistry Approaches to the Inhibition of Dipeptidyl Peptidase IV", Current Topics in Medicinal Chemistry, 2008, 8, pp. 1545-1552.
Halimi, Serge, et al. "Combination treatment in the management of type 2 diabetes: focus on vildagliptin and metformin as a single tablet" (2008) Vascular Health and Risk Management, 4(3) 481-492.
Handlon, Anthony L. "Sodium glucose co-transporter 2 (SGLT2) inhibitors as potential antidiabetic agents" (2005) =Expert Opinion on Therapeutic Patents, 15:11, 1531-1540.
Hansch, C. "Search for New Drugs, Use of Quantitative Structure—Activity Relationships (QSAR) in Drug Design" (1980) Pomona College, Clermont, CA, Translated from Khimiko-Farmatsevticheskii Zhurnal, vol. 14, No. 10, 15-30.
Harris, Maureen I. "Classification, Diagnostic Criteria, and Screening for Diabetes" (1995) Diabetes in America, 2nd Edition, pp. 15-36.
Hatsuda, Asanori., et al; A Practical Synthesis of Highly Functionalized Aryl Nitriles Through Cyanation of Aryl Bromides Employing Heterogeneous Pd/C; Tetrahedron Letters (2005) vol. 46 pp. 1849-1853; Elsevier Ltd.
He, Y. L. et al., "Bioequivalence of Vildagliptin/Metformin Combination Tablets and Coadministration of Vildagliptin and Metformin as Free Comnination in Healthy Subjects". J. Clinical Pharmacology, 2007, vol. 47, No. 9, Abstracts of the 36th Annual Meeting of the American College of Clinical Pharmacology, San Francisco, CA, Abstract 116, p. 1210.
Heise, Tim et al. "Treatment with BI 1356, a Novel and Potent DPP-IV Inhibitor Significantly Reduces Glucose Excursions after an oGTT in Patients with Type 2 Diabetes" (2007) Diabetes, Supp 1, vol. 56, 4 pgs.
Henry Ford Health System, "Chronic Kidney Disease, Clinical Practice Recommendations for Primary Care Physicians and Healthcare Providers, A Collaborative Approach", (Edition 6.0), 76 pgs.
Holst, Jens Juul et al. "Role of Incretin Hormones in the Regulaion of Insulin Secretion in Diabetic and Nondiabetic Humans" (2004) Am. J Physiol Endocrinol Metab, 287: E199-E206.
Hummel, Charles S. et al. "Glucose transport by human renal Na+/D-glucose co-transporters" (2010) Am J Physiol Cell Physiol, 34 pgs.
Hussey, Elizabeth K et al. "Safety, Pharmacokinetics and Pharmacodynamics of Remogliflozin Etabonate (SGLT2 Inhibitor) and Metformin When Co-Administered in Type 2 Diabetes Mellitus (T2DM) Patients" Diabetes, American Diabetes Association, (2009) XP00913667, vol. 58, p. A157.
Huttner, S. et al. "Safety, Tolerability, Pharmacokinetics, and Pharmacodynamics of Single Oral Doses of BI 1356, and Inhibitor of Dipeptidyl Peptidase 4, in Healthy Male Volunteers" Journal of Clinical Pharmacology (2008) V 48, pp. 1171-1178.
Hutton, Craig A., et al; A Convenient Preparation of dityrosine Via Miyaura Borylation-Suzuki Coupling of Iodotyrosine Derivatives; Tetrahedron Letters (2003) vol. 44 pp. 4895-4898; Pergamon Press.
Idris, Iskandar et al "Sodium-glucose co-transporter-2 inhibitors: an emerging new class of oral antidiabetic drug" (2009) Diabetes, Obesity and Metabolism, 11, 79-88.
Iida, Takehiko., et al; Tributylmagnesium Ate Complex-Mediated Novel Bromine-Magnesium Exchange Reaction or Selective Monosubstitution of Dibromoarenes; Tetrahedron Letters (2001) vol. 42 pp. 4841-4844; Pergamon Press.

International Search Report and Written Opinion for PCT/EP20121/053910 dated May 14, 2012.
International Search Report for PCT/EP2005/002618 dated Jun. 30, 2005.
International Search Report for PCT/EP2005/056806 dated Dec. 27, 2006.
International Search Report for PCT/EP2006/061956 dated Jul. 5, 2006.
International Search report for PCT/EP2006/061957 dated Jul. 5, 2006.
International Search Report for PCT/EP2006/062191 dated Aug. 8, 2006.
International Search Report for PCT/EP2007/062023 dated Sep. 17, 2008.
International Search Report for PCT/EP2008/060736 dated Nov. 28, 2008.
International Search Report for PCT/EP2008/060744 dated Dec. 5, 2008.
International Search Report for PCT/EP2010/051735 dated May 20, 2010.
Abdul-Ghani, Muhammad "Where does Combination Therapy with an SGLT2 Inhibitor Plus a DPP-4 Inhibitor Fit in be Management of Type 2 Diabetes?" (2015) Diabetes Care, 38, 373-375.
Abdul-Ghani, Muhammad A. et al. "Role of Sodium-Glucose Cotransporter 2 (SGLT 2) Inhibitors in the Treatment of Type 2 Diabetes" (2011) Endocrine Reviews, 32(4), 515-531.
Abstract in English for KR20070111099, Nov. 11, 2007.
Adachi, Tetsuya., et al; T-1095, A Renal Na+-Glucose Transporter Inhibitor, Improves Hyperglycemia in Streptozotocin-Induced Diabetic Rats; Metabolism (2000) vol. 49 No. 8 pp. 990-995.
Ahren B: "DPP-4 inhibitors", Best practice and research in clinical endocrinology and metabolism—New therapies for diabetes 200712 GB LNKD- DOI:10.1016/J. Beem.2007.07.005, vol. 21, No. 4, Dec. 2007, pp. 517-533.
Ahren, Bo "Dipeptidyl Peptidase-4 Inhibitors" (2007) Diabetes Care, vol. 30, No. 6, 1344-1350.
Ahren, Bo et al. "Twelve- and 52-Week Efficacy of the Dipeptidyl Peptidase IV Inhibitor LAF237 in Metformin-Treated Patients with Type 2 Diabetes" (2004) Diabetes Care, vol. 27, No. 12, 2874-2880.
Ashiya, Mona et al. "Non-insulin therapies for type 2 diabetes" (2007) Nature Reviews, Drug Discovery vol. 6, 777-778.
Augeri, David J. "Discovery and Preclinical Profile of Saxagliptin (BMS-477118): A Highly Potent, Long-Acting, Orally Active Dipeptidyl Peptidase IV Inhibitor for the Treatment of Type 2 Diabetes" J. Med. Chem. (2005) vol. 48, pp. 5025-5037.
Aulinger, B.A. et al., "Ex-4 and the DPP-IV Inhibitor Vildagliptin have Additive Effects to Suppress Food Intake in Rodents". Abstract No. 1545-P, 2008.
Ault Addison, "Techniques and experiments for organic chemistry" University Science Books, 1998, pp. 59-60.
Aulton, Michael E. "Pharmaceutics, The Science of Dosage Form Design" (2002) 2nd Edition, 404-409.
Baati, Rachid et al. "A Convenient Synthesis of 2-Tetrahydrofuranyl Ethers" (2000) Organic Letters, vol. 2, No. 4, 485-487.
Baggio, Laurie L. et al. "Biology of Incretins: GPL-1 and GIP" Gastroenterology (2007) vol. 132, 2131-2157.
Benhaddou, Rachida., et al; Tetra-n-Propylammonium Tetra-Oxoruthenate(VII): A Reagent of Choice for the Oxidation of Diversely Protected Glycopyranoses and Glycofuranoses to Lactones; Carbohydrate Research (1994) vol. 260 pp. 243-250.
Brazg, R et al. "Effect of Adding MK-0431 to Ongoing Metformin Therapy in Type 2" (2005) Diabetes, vol. 54, Suppl. 1, A3.
Brazg, R. et al: "Effect of adding sitagliptin, a dipeptidyll peptidase-4 inhibitor, to metformin on 24-h glycaemic control and beta-cell function in patients with type 2 diabetes." Diabetes, Obesity and Metabolism, Mar. 2007, vol. 9, No. 2, Mar. 2007 pp. 186-193.
Bristol-Myers Squibb Company, Label "Glucophage (metformin hydrochloride) Tablets, Glucophage XR (metformin hydrochloride) Extended-Release Tablets" Apr. 2017, 35 pgs.
British National Formulary (2008) "6. Endrocrine system" 2 pgs.
Byrn, Stephen et al. "Pharmaceutical Solids: A Strategic Approach to Regulatory Considerations" Pharmaceutical Research, vol. 12, No. 7, (1995) pp. 945-954.

(56) References Cited

OTHER PUBLICATIONS

Caira, Mino R. "Crystalline Polymorphism of Organic Compounds" (1998) Topics in Current Chemistry, vol. 198, 164-208.

Campbell, R. Keith "Rationale for Dipeptidyl Peptidase 4 Inhibitors: A New Class of Oral Agents for the Treatment of Type 2 Diabetes Mellitus" (2007) the Annals of Pharmacotherapy, vol. 41, 51-60.

CAS Registry No. 668270-12-0; STN database entered Mar. 28, 2004. 5 pgs.

Castaneda, Francisco et al. "Thioglycosides as inhibitors of hSGLT1 and hSGLT2: Potential therapeutic agents for the control of hyperglycemia in diabetes" International Journal of Medical Sciences (2007) 4(3), pp. 131-139.

Charpentier, Guillaume "Oral combination therapy for type 2 diabetes" (2002) Diabetes Metab Res Rev, vol. 18, S70-S76.

Chyan, Yau-Jan, et al. "Dipeptidyl Peptidase-IV Inhibitors: An Evolving Treatment for Tyep 2 Diabetes from the Incretin Concept" (2007) Recent Patents on Endocrine, Metabolic & Immune Drug Discovery, vol. 1, No. 1, 15-24.

Clinical Trials. "View of NCT00601250 on Jan. 25, 2008: Efficacy and Safety of BI 1356 vs Placebo added to Metformin Background Therapy in Patients with Type 2 Diabetes" Clinical Trials. Gov Archive, [Online] Jan. 25, 2008 URL:http://clinicaltrials.gov/archive/NCT00601250/2008_01_25 [retrieved on Feb. 27, 2009].

Clinical Trials. NCT00622284. "Efficacy and safety of BI 1356 in combination with metformin in patients with type 2 diabetes" ClinicalTrials.gov (Online) No. NCT00622284, Feb. 13, 2008, pp. 1-5, URL:http://clinicaltrial.gov/ct2/show/.

Clinical Trials: NCT00954447, View on Jun. 14, 2010. "Efficacy and Safety of Linagliptin in Combination with Insulin in Patients with Type 2 Diabetes". <http://clinicaltrials.gov/archive/NCT00954447/2010_06_14>.

Clinical Trials: NCT00309608. Efficacy and safety of BI 1356 in combination with metformin in patients with type2 diabetes. Boehringer Ingelheim Pharmaceuticals, Jan. 27, 2009. Clinical Trials.gov . http://clinicaltrials.gov/archive/NCT00309608/2009_01_27.

Clinical Trials: NCT00328172 "Efficacy and Safety of 3 Doses of BI1356 (Linagliptin) in Type 2 Diabetes Patients" Sponsor: Boehringer Ingelheim, Last Update Posted Mar. 14, 2014, 4 pgs.

Clinical Trials: NCT00554450 "Renal Impairment in Type 2 Diabetic Subjects" Sponsor: AstraZeneca, Last Update Posted Oct. 17, 2016, 5 pgs.

Clinical Trials: NCT00602472. "BI 1356 in combination withe metformin and a sulphonylurea in Type 2 Diabetes". DrugLib.com, Nov. 3, 2008. http://www.druglib.com/trial/08/NCT00309608.html.

Clinical Trials: NCT00622284. Efficacy and Safety of BI 1356 in Combination with Metformin in Patients with Type 2 Diabetes. Boehringer Ingelheim Pharmaceuticals, Aug. 2008. http://clinicaltrials.gov/archive/NCT00622284/2010_01_13.

Clinical Trials: NCT00798161. "Safety and efficacy of Bi 1356 Plus Metformin in Type 2 Diabetes, Factorial Design". Clinical Trials.gov archive. A Service of the U.S> National Institutes of Health. Nov. 24, 2008, pp. 1-3. http://clinicaltrials.gov/archive/NCT00798161/2008_11_24.

Clinical Trials: NCT01064414 "An Efficacy, Safety and Tolerability Stude of Canagliflozin in Patients with Type 2 Diabetes Mellitus who have Moderate Renal Impairment" Sponsor: Janssen Research & Development LLC, Last Update Posted Aug. 14, 2013, 7 pgs.

Clinical Trials: NCT01210001 "Efficacy and Safety of Empagliflozin (BI 10773) in Type 2 Diabetes Patients on a Background of Pioglitazone Alone or with Metformin" Sponsor: Boehringer Ingelheim, Last Update Posted Jun. 17, 2014, 7 pgs.

Colorcon; Opadry II Aqueous Film Coating; http://www.colorcon.com/products-formulation/all-products/film-coatings/immediate-release/opadry-ll ; Dec. 31, 2015.

Conarello, S.L. et al., "Mice lacking dipeptidyl peptidase IV are protected against obesity and insulin resistance". PNAS, May 27, 2003, vol. 100, No. 11, pp. 6825-6830.

Cornell, Susan "Vildagliptin (LAF 237): A Dipeptidyl Peptidase IV Inhibitor for the Treatment of Type 2 Diabetes Mellitus" (2006) J Pharm Technol, vol. 22, pp. 105-109.

Crepaldi, G. et al. "Dipeptidyl peptidase 4 (DPP-4) inhibitors and their role in Type 2 diabetes management" (2007) J. Endocrinol. Invest. 30: pp. 610-614.

Crepaldi, G. et al. "Dipeptidyl peptidase 4 (DPP-4) inhibitors and their role in Type 2 diabetes management" (2007) J. Endocrinol. Invest., 30, 610-614.

Deacon, Carolyn F. "Perspectives in Diabetes Therapeutic Strategies Based on Glucagon-Like Peptide 1" Diabetes, (2004) vol. 53 pp. 2181-2189.

DeFronzo, Ralph A. et al. "Combination of Empagliflozin and Linagliptin as Second-Line Therapy in Subjects with Type 2 Diabetes Inadequately Controlled on Metformin" (2015) Diabetes Care, 38, 384-393.

Derosa, Giuseppe et al. "Optimizing combination treatment in the management of type 2 diabetes" (2007) Vascular Health and Risk Management, 3(5), pp. 665-671.

Dohle, Wolfgang., et al; Copper-Mediated Cross-Coupling of Functionalized Arylmagnesium Reagents with Functionalized Alkyl and Benzylic Halides; Organic Letters (2001) vol. 3 No. 18 pp. 2871-2873.

Drucker, Daniel J. et al. "Glucagon-like peptide I stimulates insulin gene expression and increases cyclic AMP levels in a rat islet cell line" (1987) Proc. Natl. Acad. Sci. USA, vol. 84, 3434-3438.

Drug Watch "Type 2 Diabetes Mellitus" Formulary vol. 43 Aug. 2008 p. 304.

DrugBank entries for Linagliptin (Accession No: DB08882), Sitagliptin (Accession No: DB01261) and Vitagliptin '(Accession No: DB04876), downloaded Jan. 30, 2018, 12 pgs.

Eckhardt, M. et al., "3,5-dihydro-imidazo[4,5-d]pyridazin-4-ones: a class of potent DPP-4 inhibitors" Bioorganic & Medicinal Chemistry Letters, Pergamon, Elsevier Science, GB, vol. 18, No. 11, Jun. 1, 2008, pp. 3158-3162, XP022711188.

U.S. Appl. No. 15/380,272, filed Dec. 15, 2016. Non Final Office Action dated Mar. 5, 2019. 18 pgs.

Rosenstock, Julio et al. "Dual Add-on Therapy in Type 2 Diabetes Poorly Controlled with Metfromin Monotherapy: A Randomized Double-Blind Trial of Saxagliptin Plus Dapagliflozin Addition Versus Single Addition of Saxafliptin or Dapagliflozin to Metformin" (2015) Diabetes Care, vol. 38: 376-383.

Office Action dated Nov. 18, 2019, U.S. Appl. No. 15/778,294 filed May 23, 2018.

Final Office Action dated Dec. 3, 2019, U.S. Appl. No. 15/380,272 filed Dec. 15, 2016.

* cited by examiner

PHARMACEUTICAL COMPOSITIONS

The present invention relates to pharmaceutical compositions containing a fixed dose combination (FDC) comprising a DPP-4 inhibitor drug (particularly 1-[(4-methyl-quinazolin-2-yl)methyl]-3-methyl-7-(2-butyn-1-yl)-8-(3-(R)-amino-piperidin-1-yl)-xanthine, also named linagliptin) and/or a SGLT-2 inhibitor drug (particularly 1-chloro-4-(β-D-glucopyranos-1-yl)-2-[4-((S)-tetrahydrofuran-3-yloxy)-benzyl]-benzene, also named Compound "A" herein), and metformin (particularly metformin hydrochloride) in extended release form (metformin XR); processes for the preparation thereof, and their use to treat certain diseases.

In particular, the present invention relates to a pharmaceutical composition comprising a fixed dose combination of an extended release form of metformin hydrochloride, optionally seal coated, which is further coated with an immediate release form of 1-[(4-methyl-quinazolin-2-yl)methyl]-3-methyl-7-(2-butyn-1-yl)-8-(3-(R)-amino-piperidin-1-yl)-xanthine (linagliptin) and/or 1-chloro-4-(β-D-glucopyranos-1-yl)-2-[4-((S)-tetrahydrofuran-3-yloxy)-benzyl]-benzene (Compound "A").

Further, the present invention relates to a pharmaceutical composition, particularly a solid preparation (e.g. an oral solid dosage form, such as e.g. a tablet), comprising or consisting essentially of
a) an inner extended release core comprising metformin (particularly metformin hydrochloride) and one or more excipients;
b) an optional intermediate seal coating; and
c) an outer immediate release coating comprising at least one active pharmaceutical ingredient selected from
a DPP-4 inhibitor, preferably linagliptin, and
a SGLT-2 inhibitor, preferably Compound "A",
and one or more excipients.

In a more detailed aspect, the present invention relates to a pharmaceutical composition, particularly a solid preparation (e.g. an oral solid dosage form, such as a tablet) of a selected dipeptidyl peptidase-4 (DPP-4) inhibitor (preferably linagliptin, particularly in immediate release form) and metformin (particularly metformin hydrochloride) in extended release form (metformin XR). In one embodiment of this aspect, the present invention relates to a pharmaceutical composition, particularly a solid preparation (e.g. an oral solid dosage form, such as a tablet), comprising a fixed dose combination of an extended release form of metformin hydrochloride, optionally seal coated, and further coated with an immediate release form of linagliptin.

In another more detailed aspect, the present invention relates to a pharmaceutical composition, particularly a solid preparation (e.g. an oral solid dosage form, such as a tablet) of a selected SGLT-2 inhibitor (preferably 1-chloro-4-(β-D-glucopyranos-1-yl)-2-[4-((S)-tetrahydrofuran-3-yloxy)-benzyl]-benzene, particularly in immediate release form) and metformin (particularly metformin hydrochloride) in extended release form (metformin XR). In one embodiment of this aspect, the present invention relates to a pharmaceutical composition, particularly a solid preparation (e.g. an oral solid dosage form, such as a tablet), comprising a fixed dose combination of an extended release form of metformin hydrochloride, optionally seal coated, and further coated with an immediate release form of 1-chloro-4-(β-D-glucopyranos-1-yl)-2-[4-((S)-tetrahydrofuran-3-yloxy)-benzyl]-benzene.

In a further more detailed aspect, the present invention relates to a pharmaceutical composition, particularly a solid preparation (e.g. an oral solid dosage form, such as e.g. a tablet), comprising
a first component, part or composition comprising metformin (particularly metformin hydrochloride) in extended release form and one or more excipients, and
a second component, part or composition comprising a selected dipeptidyl peptidase-4 (DPP-4) inhibitor (preferably linagliptin), particularly in immediate release form, and one or more excipients.

In particular, the present invention relates to a pharmaceutical composition, particularly a solid preparation (e.g. an oral solid dosage form, such as a tablet), comprising an extended release form of metformin hydrochloride, optionally seal coated, and further coated with an immediate release form of linagliptin.

In another further more detailed aspect, the present invention relates to a pharmaceutical composition, particularly a solid preparation (e.g. an oral solid dosage form, such as e.g. a tablet), comprising
a first component, part or composition comprising metformin (particularly metformin hydrochloride) in extended release form and one or more excipients, and
a second component, part or composition comprising a selected SGLT-2 inhibitor (preferably 1-chloro-4-(β-D-glucopyranos-1-yl)-2-[4-((S)-tetrahydrofuran-3-yloxy)-benzyl]-benzene), particularly in immediate release form, and one or more excipients.

In particular, the present invention relates to a pharmaceutical composition, particularly a solid preparation (e.g. an oral solid dosage form, such as a tablet), comprising an extended release form of metformin hydrochloride, optionally seal coated, and further coated with an immediate release form of 1-chloro-4-(β-D-glucopyranos-1-yl)-2-[4-((S)-tetrahydrofuran-3-yloxy)-benzyl]-benzene.

In a yet further more detailed aspect, the present invention relates to a pharmaceutical composition, particularly a solid preparation (e.g. an oral solid dosage form, such as e.g. a tablet), comprising
a) an inner extended release core comprising metformin (particularly metformin hydrochloride) and one or more excipients,
b) an optional seal coating, and
c) an outer immediate release coating comprising a selected dipeptidyl peptidase-4 (DPP-4) inhibitor (preferably linagliptin) and one or more excipients.

In another yet further more detailed aspect, the present invention relates to a pharmaceutical composition, particularly a solid preparation (e.g. an oral solid dosage form, such as e.g. a tablet), comprising
a) an inner extended release core comprising metformin (particularly metformin hydrochloride) and one or more excipients,
b) an optional seal coating, and
c) an outer immediate release coating comprising a selected SGLT-2 inhibitor (preferably 1-chloro-4-(β-D-glucopyranos-1-yl)-2-[4-((S)-tetrahydrofuran-3-yloxy)-benzyl]-benzene) and one or more excipients.

Particularly, the pharmaceutical compositions of this invention comprise an inner core formulation of metformin hydrochloride comprising a swellable and/or extended release material.

In an embodiment, the pharmaceutical compositions of this invention comprise an inner extended release core which is a formulation (e.g. matrix fomulation) comprising metformin hydrochloride, a swellable and/or extended release material, and one or more further excipients.

Particularly, the pharmaceutical compositions of this invention comprise an outer coat of active pharmaceutical ingredient (API) (linagliptin and/or 1-chloro-4-(β-D-glucopyranos-1-yl)-2-[4-((S)-tetrahydrofuran-3-yloxy)-benzyl]-benzene) in an immediate release polymer film.

Further, the present invention relates to a coating process (e.g. coating technology and processing conditions) and immediate release coating formulations of active pharmaceutical ingredients (API) in low doses (typically in doses of 0.5 to 25 mg) on top of tablet cores comprising active pharmaceutical ingredients (API) in high doses (typically in doses of 500-1500 mg) preferably, but not exclusively on extended release tablets. Anyhow, essential parts of the formulation and the process of this invention may be also applicable to any other fixed dose combination with the described setting.

An aim of the present invention is to provide a pharmaceutical composition comprising a combination of a selected DPP-4 inhibitor (preferably linagliptin, particularly in immediate release form), and metformin (particularly metformin hydrochloride) in extended release form. Another aim of the present invention is to provide a pharmaceutical composition comprising a combination of a selected SGLT-2 inhibitor (preferably 1-chloro-4-(β-D-glucopyranos-1-yl)-2-[4-((S)-tetrahydrofuran-3-yloxy)-benzyl]-benzene, particularly in immediate release form), and metformin (particularly metformin hydrochloride) in extended release form.

The objectives of are to identify suitable formulations and processing conditions, such as e.g. of a coat of linagliptin or of 1-chloro-4-(β-D-glucopyranos-1-yl)-2-[4-((S)-tetrahydrofuran-3-yloxy)-benzyl]-benzene on top metformin XR cores, providing adequate:

Chemical stability of the API (particularly linagliptin) in the API film coat,

Assay of linagliptin or 1-chloro-4-(β-D-glucopyranos-1-yl)-2-[4-((S)-tetrahydrofuran-3-yloxy)-benzyl]-benzene in the API film-coat (e.g. 95-105%), Content uniformity of linagliptin or 1-chloro-4-(β-D-glucopyranos-1-yl)-2-[4-((S)-tetrahydrofuran-3-yloxy)-benzyl]-benzene (e.g. RSD<3%) in the API film-coat, Low defect rate of the API-film during film coating process, Fast dissolution of the API from the API film-coat and no changes of XR Metformin HCl dissolution, due to the API coating with immediate release of linagliptin or 1-chloro-4-(β-D-glucopyranos-1-yl)-2-[4-((S)-tetrahydrofuran-3-yloxy)-benzyl]-benzene, Processing aspects of coating process/technology, processing conditions and immediate release API (linagliptin or Compound "A") coating formulations (API film coat), Processing aspects of coating process/technology, processing conditions and immediate release API (linagliptin or Compound "A") coating formulations on top of metformin extended release tablets.

A particular objective of the present invention is to provide a pharmaceutical composition and suitable coating process with very broad range of drug substance (linagliptin or Compound "A")/drug substance (metformin) ratio: 1:400-1:40. And the ratio of very low dosed API, e.g. linagliptin with 1 mg or 2.5 mg to very high dosed metformin with 1000 mg and more. And the suitable immediate release dissolution of the low dosed API with high dosed extended release metformin.

The unit dosage strength of the metformin hydrochloride for incorporation into the fixed-dose combination of the present invention is 500, 750, 850 or 1000 milligrams, or even more (e.g. 1500 mg).

These unit dosage strengths of metformin hydrochloride represent the dosage strengths approved in the U.S. for marketing to treat Type 2 diabetes.

The unit dosage strength of linagliptin for incorporation into the fixed-dose combination of the present invention is 2.5 or 5 milligrams, or even less (e.g. 0.5 mg or 1 mg).

The unit dosage strength of 1-chloro-4-(β-D-glucopyranos-1-yl)-2-[4-((S)-tetrahydrofuran-3-yloxy)-benzyl]-benzene for incorporation into the fixed-dose combination of the present invention is 5, 10, 12.5 or 25 milligrams.

Specific embodiments of dosage strengths for linagliptin and metformin hydrochloride in the fixed-dose combinations of the present invention are the following:

(1) 5 milligrams of linagliptin and 1000 milligrams metformin hydrochloride;

(2) 2.5 milligrams of linagliptin and 1000 milligrams metformin hydrochloride;

(3) 2.5 milligrams of linagliptin and 750 milligrams metformin hydrochloride.

Specific embodiments of dosage strengths for 1-chloro-4-(β-D-glucopyranos-1-yl)-2-[4-((S)-tetrahydrofuran-3-yloxy)-benzyl]-benzene and metformin hydrochloride in the fixed-dose combinations of the present invention are the following:

(1) 25 milligrams of 1-chloro-4-(β-D-glucopyranos-1-yl)-2-[4-((S)-tetrahydrofuran-3-yloxy)-benzyl]-benzene and 1000 milligrams metformin hydrochloride;

(2) 12.5 milligrams of 1-chloro-4-(β-D-glucopyranos-1-yl)-2-[4-((S)-tetrahydrofuran-3-yloxy)-benzyl]-benzene and 1000 milligrams metformin hydrochloride;

(3) 12.5 milligrams of 1-chloro-4-(β-D-glucopyranos-1-yl)-2-[4-((S)-tetrahydrofuran-3-yloxy)-benzyl]-benzene and 750 milligrams metformin hydrochloride;

(4) 10 milligrams of 1-chloro-4-(β-D-glucopyranos-1-yl)-2-[4-((S)-tetrahydrofuran-3-yloxy)-benzyl]-benzene and 1000 milligrams metformin hydrochloride;

(5) 10 milligrams of 1-chloro-4-(β-D-glucopyranos-1-yl)-2-[4-((S)-tetrahydrofuran-3-yloxy)-benzyl]-benzene and 750 milligrams metformin hydrochloride;

(6) 5 milligrams of 1-chloro-4-(β-D-glucopyranos-1-yl)-2-[4-((S)-tetrahydrofuran-3-yloxy)-benzyl]-benzene and 1000 milligrams metformin hydrochloride;

(7) 5 milligrams of 1-chloro-4-(β-D-glucopyranos-1-yl)-2-[4-((S)-tetrahydrofuran-3-yloxy)-benzyl]-benzene and 750 milligrams metformin hydrochloride.

(a) Metformin part:

The first part in the present invention is a part (composition, particularly solid composition, e.g. a solid pharmaceutical composition for oral administration, e.g. tablet) comprising metformin (particularly metformin hydrochloride) in extended release form, particularly an extended release formulation of metformin.

Exemplary extended release formulations of metformin are disclosed in U.S. Pat. No. 6,340,475; U.S. Pat. No. 6,488,962; U.S. Pat. No. 6,635,280; U.S. Pat. No. 6,723,340; U.S. Pat. No. 7,780,987; U.S. Pat. No. 6,866,866; U.S. Pat. No. 6,495,162; U.S. Pat. No. 6,790,459; U.S. Pat. No. 6,866,866; U.S. Pat. No. 6,475,521; and U.S. Pat. No. 6,660,300; the disclosures of which are incorporated herein in their entireties.

A particular extended release formulation of metformin is described in U.S. Pat. No. 6,723,340, the disclosure of which is incorporated herein in its entirety.

In an embodiment, the fixed-dose combination products of the present invention comprise—as first part—an inner core matrix formulation with metformin hydrochloride dispersed therein, said matrix formulation containing an extended release material. The matrix formulation is compressed into a tablet form.

In particular, the fixed-dose combination products of the present invention comprise—as first part—an inner core extended release formulation comprising metformin hydrochloride, hydroxypropyl methylcellulose (hypromellose), polyethylene oxide, microcrystalline cellulose, and magnesium stearate.

A particular extended release formulation of metformin is described in U.S. Pat. No. 6,723,340 as follows:

In an embodiment, the extended release material of the matrix comprises poly(ethylene oxide) and/or hydroxypropyl methylcellulose (HPMC), preferably a combination of poly(ethylene oxide) and hydroxypropyl methylcellulose (HPMC), preferably at a weight ratio that causes the matrix to swell upon contact with gastric fluid to a size large enough to provide gastric retention.

The poly(ethylene oxide) component of the matrix may limit initial release of the drug and may impart gastric retention through swelling. The hydroxypropyl methylcellulose (HPMC) component may lower the amount of poly(ethylene oxide) required while still allowing the swelling to occur.

Preferably, the poly(ethylene oxide) has a viscosity average molecular weight of from about 2,000,000 to about 10,000,000 daltons, more preferably from about 4,000,000 to about 7,000,000 daltons.

Preferably, the hydroxypropyl methylcellulose (HPMC) has a viscosity of from about 4,000 centipoise to about 200,000 centipoise, more preferably from about 50,000 to about 200,000 centipoise, even more preferably 80,000 centipoise to about 120,000 centipoise, measured as a 2% solution in water.

More preferably, the poly(ethylene oxide) has a viscosity average molecular weight of from about 4,000,000 to about 7,000,000 daltons, and the hydroxypropyl methylcellulose (HPMC) has a viscosity of from about 80,000 centipoise to about 120,000 centipoise, measured as a 2% solution in water.

In an embodiment, the weight ratio of the poly(ethylene oxide) to hydroxypropyl methylcellulose (HPMC) is within the range from about 1:3 to 3:1, preferably 1:2 to 2:1.

In a further embodiment, the weight ratio of the poly(ethylene oxide) and hydroxypropyl methylcellulose (HPMC) in combination constitutes from about 15% to about 90%, or from about 30% to about 65%, or from about 40% to about 50%, by weight of the metformin part.

Tablet cores in accordance with this invention can be prepared by common tabletting methods that involve mixing, comminution, and fabrication steps commonly practiced by and well known to those skilled in the art of manufacturing drug formulations. Examples of such techniques are:

(1) Direct compression using appropriate punches and dies, typically fitted to a suitable rotary tabletting press;
(2) Injection or compression molding;
(3) Granulation by fluid bed, by low or high shear granulation, or by roller compaction, followed by compression; and
(4) Extrusion of a paste into a mold or to an extrudate to be cut into lengths.

When tablets are made by direct compression, the addition of lubricants may be helpful and is sometimes important to promote powder flow and to prevent breaking of the tablet when the pressure is relieved. Examples of typical lubricants are magnesium stearate (in a concentration of from 0.25% to 3% by weight, preferably about 1% or less by weight, in the powder mix), stearic acid (0.5% to 3% by weight), and hydrogenated vegetable oil (preferably hydrogenated and refined triglycerides of stearic and palmitic acids at about 1% to 5% by weight, most preferably about 2% by weight).

Additional excipients may be added, such as e.g. granulating aids (e.g. low molecular weight HPMC at 2-5% by weight), binders (e.g. microcrystalline cellulose), and additives to enhance powder flowability, tablet hardness, and tablet friability and to reduce adherence to the die wall.

An exemplary extended release metformin tablet core comprises metformin hydrochloride, a combination of poly(ethylene oxide) and hydroxypropyl methylcellulose (e.g. Methocel K100M) as a matrix for a swellable extended release tablet, microcrystalline cellulose as binder, low molecular weight hydroxypropyl methylcellulose (e.g. Methocel E5) as granulating aid, and magnesium stearate as lubricant.

The composition of a representative metformin core tablet is provided as follows:

metformin hydrochloride, e.g. 49.97% by weight of the first part,
poly(ethylene oxide), e.g. 26.50% by weight of the first part,
hydroxypropyl methylcellulose (e.g. Methocel K100M), e.g. 16.08% by weight of the first part,
microcrystalline cellulose, e.g. 4.99% by weight of the first part,
low molecular weight hydroxypropyl methylcellulose (e.g. Methocel E5), e.g. 1.70% by weight of the first part, and
magnesium stearate, e.g. 0.75% by weight of the first part.

Tablets may be formulated by dry blending a granulation comprising metformin hydrochloride and low molecular weight HPMC (e.g. Methocel E5) and the remaining excipients listed above, followed by pressing on a tablet press.

Such an extended release matrix formulation of metformin is disclosed in U.S. Pat. No. 6,723,340 (e.g. Example 3), the disclosure of which is incorporated herein in its entirety.

As further example of a lubricant sodium stearyl fumarate may be mentioned (e.g. at about 0.25-3% by weight).

In a further embodiment, the metformin extended release formulation allows for targeted, controlled delivery of metformin to the upper gastrointestinal (GI) tract. In a further embodiment, the metformin extended release formulation is a hydrogel matrix system and contains a swelling hydrophilic polymer and further excipients, which may allow the metformin tablet core to be retained in the stomach ('gastric retention') for approximately eight to nine hours. During this time, the tablet core's metformin is steadily delivered to the upper GI tract at the desired rate and time, without potentially irritating 'burst' of drug. This gradual, extended release typically allows for more of the metformin drug to be absorbed in the upper GI tract and minimizes the amount of drug that passes through to the lower GI tract.

(b1) Linagliptin Part:

In one variant, the second part in the present invention is a part (composition, particularly film coat) comprising linagliptin in immediate release form.

In a particular embodiment, the fixed-dose combination products of the present invention comprise—as second part—a film coat formulation of linagliptin, said film coat formulation comprising linagliptin, a stabilizer for stabilizing linagliptin (e.g. a basic and/or nucleophilic excipient, preferably L-arginine as stabilizer), a film-coating agent (such as e.g. hydroxypropyl methylcellulose, e.g. Hypromellose 2910, Methocel E5, or Methocel E15), a plasticizer (such as e.g. polyethylene glycol, e.g. Macrogol 400, 6000 or 8000, or propylene glycol), and, optionally, a glidant (such as e.g. talc).

In an embodiment, the weight ratio of the L-arginine to linagliptin is within the range from about 2:1 to about 1:1, up to about 0.2:1.

The composition of a representative linagliptin containing film coat is provided as follows:
  linagliptin, e.g. 2.5 mg or 5 mg;
  L-arginine, e.g. depending from need of stabilizer amount, e.g. in the range from about 0.5 mg to about 10 mg (e.g. 5 mg);
  hydroxypropyl methylcellulose (e.g. Methocel E5, Methocel E15, or Pharmacoat 603 or 606), e.g. from about 25 mg to about 40 mg (especially from 34.5 mg to 38 mg, or 34.5 mg);
  polyethylene glycol (e.g. Macrogol 400, 6000 or 8000), e.g. from about 0 to about 12 mg;
  propylene glycol, e.g. from about 0 mg to about 15 mg (especially 9 mg); and
  talc, e.g. from about 0 mg to about 15 mg (especially 9 mg).

Depending from need of stabilizer the amount of L-arginine may be in the range from 0.5 mg to 10 mg. With different dose and different arginine amount, the arginine amount may be substitued by hydroxypropyl methylcellulose (HPMC).

In an embodiment, polyethylene glycol and propylene glycol are mutually exclusive in above composition, i.e. if polyethylene glycol is present then propylene glycol is absent, or if propylene glycol is present then polyethylene glycol is absent.

The composition of a representative linagliptin containing film coat suspension further comprises water, e.g. from about 240 mg to about 1440 mg, especially in the range from 904 mg to 1440 mg. The total solids concentration of the suspension is from about 4% to about 12.5% w/w, especially from 4% to 6% w/w. Viscosity may be from about 10 mPas to 110 mPas (e.g. 46-56 mPas).

The sum solids of the linagliptin coating suspension is from about 50 mg to about 120 mg. For example, the sum solids is 60 mg of solid amount of the film coating suspension for 2.5 mg linagliptin, and 120 mg sum solid amount of the film coating suspension for 5 mg linagliptin. Therefore with the same formulation of linagliptin and double coating time (i.e. double amount of coating suspension) it is possible to prepare the higher dose range of linagliptin. Hence different dosage strengths can be achieved by altering coating (spraying) times.

(b2) 1-Chloro-4-(β-D-glucopyranos-1-yl)-2-[4-((S)-tetrahydrofuran-3-yloxy)-benzyl]-benzene part:

In another variant, the second part in the present invention is a part (composition, particularly film coat) comprising 1-chloro-4-(β-D-glucopyranos-1-yl)-2-[4-((S)-tetrahydrofuran-3-yloxy)-benzyl]-benzene in immediate release form.

In another particular embodiment, the fixed-dose combination products of the present invention comprise—as second part—a film coat formulation of 1-chloro-4-(β-D-glucopyranos-1-yl)-2-[4-((S)-tetrahydrofuran-3-yloxy)-benzyl]-benzene, said film coat formulation comprising 1-chloro-4-(β-D-glucopyranos-1-yl)-2-[4-((S)-tetrahydrofuran-3-yloxy)-benzyl]-benzene, a film-coating agent (such as e.g. hydroxypropyl methylcellulose, e.g. Hypromellose 2910, Methocel E5, or Methocel E15), a plasticizer (such as e.g. polyethylene glycol, e.g. Macrogol 400, 6000 or 8000, or propylene glycol), and, optionally, a glidant (such as e.g. talc).

The composition of a representative 1-chloro-4-(β-D-glucopyranos-1-yl)-2-[4-((S)-tetrahydrofuran-3-yloxy)-benzyl]-benzene containing film coat is provided as follows:
  1-chloro-4-(β-D-glucopyranos-1-yl)-2-[4-((S)-tetrahydrofuran-3-yloxy)-benzyl]-benzene, e.g. 5 mg, 10 mg, 12.5 mg or 25 mg;
  optionally, L-arginine, e.g. from about 5 mg to about 25 mg;
  hydroxypropyl methylcellulose (e.g. Methocel E5, Methocel E15, or Pharmacoat 603 or 606), e.g. from about 25 mg to about 40 mg (especially from 34.5 mg to 38 mg, or 34.5 mg);
  polyethylene glycol (e.g. Macrogol 400, 6000 or 8000), e.g. from about 0 to about 12 mg;
  propylene glycol, e.g. from about 0 mg to about 15 mg (especially 9 mg); and
  talc, e.g. from about 0 mg to about 15 mg (especially 9 mg).

With different dose and different arginine amount, the arginine amount may be substitued by hydroxypropyl methylcellulose (HPMC).

In an embodiment, polyethylene glycol and propylene glycol are mutually exclusive in above composition, i.e. if polyethylene glycol is present then propylene glycol is absent, or if propylene glycol is present then polyethylene glycol is absent.

The composition of a representative 1-chloro-4-(β-D-glucopyranos-1-yl)-2-[4-((S)-tetrahydrofuran-3-yloxy)-benzyl]-benzene containing film coat suspension further comprises water, e.g. from about 240 mg to about 1440 mg, especially in the range from 904 mg to 1440 mg. The total solids concentration of the suspension is from about 4% to about 12.5% w/w, especially from 4% to 6% w/w.

The sum solids of the 1-chloro-4-(β-D-glucopyranos-1-yl)-2-[4-((S)-tetrahydrofuran-3-yloxy)-benzyl]-benzene coating suspension is from about 50 mg to about 120 mg. For example, the sum solids is 60 mg of solid amount of the film coating suspension for 12.5 mg 1-chloro-4-(β-D-glucopyranos-1-yl)-2-[4-((S)-tetrahydrofuran-3-yloxy)-benzyl]-benzene, and 120 mg sum solid amount of the film coating suspension for 25 mg 1-chloro-4-(β-D-glucopyranos-1-yl)-2-[4-((S)-tetrahydrofuran-3-yloxy)-benzyl]-benzene. Therefore with the same formulation of 1-chloro-4-(β-D-glucopyranos-1-yl)-2-[4-((S)-tetrahydrofuran-3-yloxy)-benzyl]-benzene and double coating time (i.e. double amount of coating suspension) it is possible to prepare the higher dose range of 1-chloro-4-(β-D-glucopyranos-1-yl)-2-[4-((S)-tetrahydrofuran-3-yloxy)-benzyl]-benzene. Hence different dosage strengths can be achieved by altering coating (spraying) times.

L-Arginine is preferably necessary for the stabilization of linagliptin. Alternatively, a seal coat may be used between the metformin XR core and the linagliptin-containing film coat. In one embodiment, a seal coat is present between the metformin XR core and the linagliptin-containing film coat (optionally further containing L-arginine). In another embodiment, the seal coat is absent between the metformin XR core and the linagliptin-containing film coat (preferably further containing L-arginine).

For Compound "A" preferably no arginine is necessary. For Compound "A" the seal coating of metformin XR cores is optional. In one embodiment, a seal coat is present between the metformin XR core and the Compound "A" containing film coat. In another embodiment, the seal coat is absent between the metformin XR core and the Compound "A" containing film coat.

Alternatively, for the API (linagliptin or Compound "A") containing film coat, a film coat comprising a mixture of hydroxypropylcellulose and hydroxypropyl methylcellulose, or a mixture of polyvinyl alcohol (PVA) and polyethylene glycol (PEG); or a commercial film-coat such as Opadry®, Opadry II® or other Opardy IR film coat, which are formulated powder blends provided by Colorcon, may be used. With Opadry II or PVA based API coating higher solid concentrations and shorter coating time durations are possible, therefore it works in a range of 10-30%, especially 20% solid concentration. This higher solid concentration, e.g. 20%, typically results in a shorter coating time, e.g. 2-5 hours.

For example, further versions of API-containing film coat compositions comprising one or more of the following ingredients of Tables 1 or 2 may be provided, e.g. as follows from Tables 1 or 2:

TABLE 1

Example formulations for API-coating of linagliptin on top of metformin XR cores

| Composition (% w/w) | PEG-containing version (e.g. 2.5 mg API) | PEG-containing version (reduced arginine) (e.g. 5 mg API) | PG-containing version (low DL) (e.g. 2.5 mg API) | PG-containing version (high DL) (e.g. 2.5 mg API) | Further version (e.g. 2.5 mg API) | Further version (e.g. 5 mg API) |
| --- | --- | --- | --- | --- | --- | --- |
| Linagliptin | 4.20 | 4.39 | 4.55 | 5.29 | 4.16 | 4.16 |
| HPMC (e.g Pharmacoat 615)* | 67.23 | 70.18 | 72.73 | 70.55 | — | — |
| HPMC (e.g Methocel E5) | — | — | — | — | 57.5 | 57.5 |
| Polyethylene glycol (e.g. PEG 6000) | 20.17 | 21.05 | — | — | 15 | 15 |
| Propylene glycol | — | — | 3.64 | 3.53 | — | — |
| L-Arginine | 8.40 | 4.39 | 9.09 | 10.58 | 8.33 | 8.33 |
| Talc | — | — | 10.00 | 10.05 | 15 | 15 |
| Purified water | ** | ** | ** | ** | ** | ** |
| Total | 100.00 | 100.00 | 100.00 | 100.00 | 100.00 | 100.00 |
| Solid content of suspension (%) | 5.95 | 5.70 | 5.50 | 5.67 | 4.0 | 4.0 |

*Alternative Methocel E15
**Solvent is a volatile component, which does not remain in the final product In one embodiment of the API coatings of this invention, the film-coating agent used is highly viscous.

In another embodiment of the API coatings of this invention, the film-coating agent used is low viscous.

TABLE 2

Further Example formulations for API-coating of linagliptin on top of metformin XR cores:

| Composition (% w/w) | PEG-containing version (e.g. 2.5 mg API) | PEG-containing version (reduced arginine) (e.g. 5 mg API) | PG-containing version (low DL) (e.g. 2.5 mg API) | PG-containing version (high DL) (e.g. 2.5 mg API) |
| --- | --- | --- | --- | --- |
| Linagliptin | 4.20 | 4.39 | 4.55 | 5.29 |
| HPMC (e.g. Pharmacoat 615) | 67.23 | 70.18 | 72.73 | 70.55 |
| Polyethylene glycol (e.g. PEG 6000) | 20.17 | 21.05 | — | — |
| Propylene glycol | — | — | 3.64 | 3.53 |
| L-Arginine | 8.40 | 4.39 | 9.09 | 10.58 |
| Talc | — | — | 10.00 | 10.05 |
| Purified water | ** | ** | ** | ** |
| Total | 100.00 | 100.00 | 100.00 | 100.00 |
| Solid content of suspension (%) | 5.95 | 5.70 | 5.50 | 5.67 |

**Solvent is a volatile component, which does not remain in the final product

Film coating suspensions/solutions of API (linagliptin or Compound "A") according to this invention can be prepared by common methods, such as follows:

The film-coating agent hydroxypropyl methylcellulose (HPMC), the plasticizer polyethylene glycol (PEG) (e.g. Macrogol 400, 6000 or 8000) or, as alternative plasticizer, propylene glycol (PG) and water are dissolved and mixed by a suitable mixer (e.g. by propeller mixer) to produce the API-free coating solution. Optionally, the glidant talc suspended in water is added and the obtained suspension is homogenized. Talc may be used optionally.

The API (linagliptin or Compound "A") and—preferably in case of linagliptin—the stabilizer L-arginine are dissolved or suspended in water and added to the aqueous solution of HPMC, PEG or PG, and, optional talc, and dispersed by a suitable mixer (e.g. by propeller mixer) to provide the API coating suspension.

Alternatively, the film-coating agent hydroxypropyl methylcellulose (HPMC) and water are dissolved and mixed by a suitable mixer (e.g. by Ultraturrax).

The stabilizer L-arginine (which is present in case of linagliptin, and may be absent in case of Compound "A"), the plasticizer polyethylene glycol (PEG) (e.g. Macrogol 400, 6000 or 8000) or propylene glycol (PG), optional talc, and water are dispersed, e.g. by homogenization using e.g. ultra turrax.

After degassing of the HPMC solution (or directly after manufacturing of the HPMC solution), the aqueous suspension of PEG or PG, optional L-arginine and optional talc are added to the aqueous HPMC solution and mixed/homogenized.

The API (linagliptin or Compound "A") is dissolved or suspended in water and added to the aqueous solution of HPMC, PEG or PG, optional L-arginine and optional talc to provide the API coating suspension.

The film-coating operation is carried out in a conventional film coater. The API (linagliptin or Compound "A") coating suspension/solution are coated at metformin XR cores via coating process.

Preliminary preheating of the cores may be necessary, due to need of equilibrium of water amount of the cores.

The spray rate and air flow through the coating pan is adjusted to produce a uniform coating and coverage of the entire width of the tablet bed. The amount of the coating suspension applied can be controlled by percent weight gain of tablet cores and typically ranges from about 4 to about 12.5%.

In one aspect, this range results in linagliptin drug assay close to the desired 2.5 mg or 5 mg with a standard deviation of about 2-4% for content uniformity assay of linagliptin. The duration of the coating step is about 4-10 hours. The duration of the coating step depends on batch size, process parameters like spray rate and solid concentrations of the coating suspension.

In another aspect, this range results in Compound "A" drug assay close to the desired 5 mg, 12.5 mg, 10 mg or 25 mg with a standard deviation of about 2-4% for content uniformity assay of Compound "A". The duration of the coating step is about 4-10 hours. The duration of the coating step depends on batch size, process parameters like spray rate and solid concentrations of the coating suspension.

The API coating suspension is applied to the tablet cores containing the metformin XR formulation and the amount of solids deposited in the API film layer is controlled to achieve the desired API doses.

The weight of the cores and film coated tablets may be controlled by percent weight gain during the coating process. Instead of or in addition to weight gain method a PAT method, e.g. online NIR or Raman method for end point detection of assay of API may be used.

An optional seal coat may separate the metformin XR core from the API-containing film coat. Typically, for the preparation of film-coated tablets a coating suspension is prepared and the tablet cores may be coated with the seal coating suspension using standard film coater.

The film coating solvent is a volatile component, which does not remain in the final product. A typical seal film-coat comprises a film coating agent, a plasticizer, and, optionally, a glidant, one or more pigments and/or colors.

The metformin XR core may be seal coated using a seal coating agent (and a plasticizer), such as with a mixture of hydroxypropylcellulose and hydroxypropyl methylcellulose, a mixture of polyvinyl alcohol (PVA) and polyethylene glycol (PEG), a mixture of hydroxypropyl methylcellulose and either polyethylene glycol (PEG) or propylene glycol (PG), or any other suitable immediate-release film-coating agent(s). A commercial film-coat is Opadry®, Opadry II® or other Opardy IR film coat, which are formulated powder blend provided by Colorcon. Optionally the seal coat may further comprise a glidant.

The final pharmaceutical compositions of the present invention are tablets. Such tablets may be further film-coated with a final film over-coat, such as with a mixture of hydroxypropylcellulose and hydroxypropyl methylcellulose containing titanium dioxide and/or other coloring agents, such as iron oxides, dyes, and lakes; a mixture of polyvinyl alcohol (PVA) and polyethylene glycol (PEG) containing titanium dioxide and/or other coloring agents, such as iron oxides, dyes, and lakes; a mixture of hydroxypropyl methylcellulose and either polyethylene glycol (PEG) or propylene glycol (PG) containing titanium dioxide and/or other coloring agents, such as iron oxides, dyes, and lakes; or any other suitable immediate-release film-coating agent(s). The coat may provide taste masking and additional stability to the final tablet. A commercial film-coat is Opadry®, Opadry II® or other Opardy IR film coat, which are formulated powder blend provided by Colorcon.

Preferably, for the preparation of film-coated tablets a coating suspension is prepared and the tablet cores are coated with the coating suspension, typically for the API-free film over-coat to a weight gain of about 2-4%, preferably about 3%, using standard film coater.

The film coating solvent is a volatile component, which does not remain in the final product. A typical film-coat comprise a film coating agent, a plasticizer, and, optionally, a glidant, one or more pigments and/or colors. For example, the film coat may comprise hydroxypropylmethylcellulose (HPMC), propylene glycol or polyethylene glycol, talc and, optionally, titanium dioxide and/or iron oxide (e.g. iron oxide yellow and/or red).

The pharmaceutical tablet compositions of the present invention may also contain one or more additional formulation ingredients selected from a wide variety of excipients known in the pharmaceutical formulation art. According to the desired properties of the pharmaceutical composition, any number of ingredients may be selected, alone or in combination, based upon their known uses in preparing tablet compositions. Such ingredients include, but are not limited to, diluents, compression aids, glidants, disintegrants, lubricants, flavors, flavor enhancers, sweeteners, and preservatives.

The term "tablet" as used herein is intended to encompass compressed pharmaceutical dosage formulations of all shapes and sizes.

The present invention also provides methods particularly for treating Type 2 diabetes by orally administering to a host in need of such treatment a therapeutically effective amount of one of the fixed-dose combination pharmaceutical compositions of the present invention. In one embodiment the host in need of such treatment is a human. In another embodiment the pharmaceutical composition is in the dosage form of a tablet. The pharmaceutical compositions comprising the fixed-dose combination may be administered once-daily (QD), twice-daily (BID), thrice-daily (TID), or four-times daily.

MANUFACTURE AND POLYMORPH

The term "linagliptin" as employed herein refers to linagliptin, a pharmaceutically acceptable salt thereof, a hydrate or solvate thereof, or a polymorphic form thereof. Crystalline forms are described in WO 2007/128721. Preferred crystalline forms are the polymorphs A and B described therein. In particular, linagliptin is the free base 1-[(4-methyl-quinazolin-2-yl)methyl]-3-methyl-7-(2-butyn-1-yl)-8-(3-(R)-amino-piperidin-1-yl)-xanthine. As linagliptin or a pharmaceutically acceptable salt thereof, linagliptin is preferred. Methods for the manufacture of linagliptin are described in the patent applications WO 2004/018468 and WO 2006/048427 for example.

1-[(4-Methyl-quinazolin-2-yl)methyl]-3-methyl-7-(2-butyn-1-yl)-8-(3-(R)-amino-piperidin-1-yl)-xanthine (linagliptin)

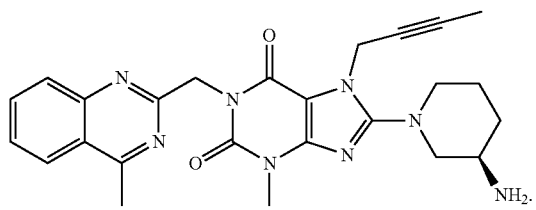 [SMILES: CC#CCn1c(N2CCC[C@@H](N)C2)nc2c1c(=O)n(Cc1nc(C)c3ccccc3n1)c(=O)n2C]

According to this invention, it is to be understood that the definition of the SGLT2 inhibitor, in particular 1-chloro-4-(β-D-glucopyranos-1-yl)-2-[4-((S)-tetrahydrofuran-3-yloxy)-benzyl]-benzene (Compound "A"), also comprises its hydrates, solvates and polymorphic forms thereof, and prodrugs thereof. With regard to the preferred 1-chloro-4-(β-D-glucopyranos-1-yl)-2-[4-((S)-tetrahydrofuran-3-yloxy)-benzyl]-benzene an advantageous crystalline form is described in the international patent applications WO 2006/117359 which hereby is incorporated herein in its entirety. This crystalline form possesses good solubility properties which enable a good bioavailability of the SGLT2 inhibitor. Furthermore, the crystalline form is physico-chemically stable and thus provides a good shelf-life stability of the pharmaceutical composition.

1-Chloro-4-(β-D-glucopyranos-1-yl)-2-[4-((S)-tetrahydrofuran-3-yloxy)-benzyl]-benzene (Compound "A")

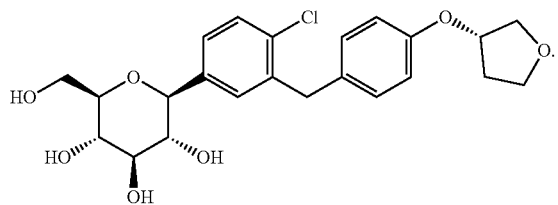 [SMILES: OC[C@H]1O[C@@H](c2ccc(Cl)c(Cc3ccc(O[C@H]4CCOC4)cc3)c2)[C@H](O)[C@@H](O)[C@@H]1O]

Methods for the manufacture of SGLT2 inhibitors according to this invention and of prodrugs thereof are known to the one skilled in the art. Advantageously, the compounds according to this invention can be prepared using synthetic methods as described in the literature, including patent applications as cited hereinbefore. Preferred methods of manufacture, in particular of 1-chloro-4-(β-D-glucopyranos-1-yl)-2-[4-((S)-tetrahydrofuran-3-yloxy)-benzyl]-benzene, are described in the WO 2006/120208.

For avoidance of any doubt, the disclosure of each of the foregoing documents cited above in connection with the specified SGLT2 or DPP-4 inhibitors is specifically incorporated herein by reference in its entirety.

INDICATIONS

As described herein by the administration of the pharmaceutical composition according to this invention, therapeutic effects can be achieved, which make it useful for treating and/or preventing certain diseases, disorders or conditions, such as e.g. those described herein.

Therefore, a treatment or prophylaxis according to this invention is advantageously suitable in those patients in need of such treatment or prophylaxis who are diagnosed of one or more of the conditions selected from the group consisting of overweight and obesity, in particular class I obesity, class II obesity, class III obesity, visceral obesity and abdominal obesity. In addition a treatment or prophylaxis according to this invention is advantageously suitable in those patients in which a weight increase is contraindicated. The pharmaceutical composition as well as the methods according to the present invention allow a reduction of the HbA1c value to a desired target range, for example <7% and preferably <6.5%, for a higher number of patients and for a longer time of therapeutic treatment compared with a corresponding monotherapy.

The pharmaceutical composition according to this invention and in particular the active ingredients therein exhibits a very good efficacy with regard to glycemic control, in particular in view of a reduction of fasting plasma glucose, postprandial plasma glucose and/or glycosylated hemoglobin (HbA1c). By administering a pharmaceutical composition according to this invention, a reduction of HbA1c equal to or greater than preferably 0.5%, even more preferably equal to or greater than 1.0% can be achieved and the reduction is particularly in the range from 1.0% to 2.0%.

Furthermore, the method and/or use according to this invention is advantageously applicable in those patients who show one, two or more of the following conditions:

(a) a fasting blood glucose or serum glucose concentration greater than 110 mg/dL, in particular greater than 125 mg/dL;

(b) a postprandial plasma glucose equal to or greater than 140 mg/dL;

(c) an HbA1c value equal to or greater than 6.5%, in particular equal to or greater than 7.0%, especially equal to or greater than 7.5%, even more particularly equal to or greater than 8.0%.

The present invention also discloses the use of the pharmaceutical composition for improving glycemic control in patients having type 2 diabetes or showing first signs of pre-diabetes. Thus, the invention also includes diabetes prevention. If therefore a pharmaceutical composition according to this invention is used to improve the glycemic control as soon as one of the above-mentioned signs of pre-diabetes is present, the onset of manifest type 2 diabetes mellitus can be delayed or prevented.

Furthermore, the pharmaceutical composition according to this invention is particularly suitable in the treatment of patients with insulin dependency, i.e. in patients who are treated or otherwise would be treated or need treatment with an insulin or a derivative of insulin or a substitute of insulin or a formulation comprising an insulin or a derivative or substitute thereof. These patients include patients with diabetes type 2 and patients with diabetes type 1.

Therefore, according to a preferred embodiment of the present invention, there is provided a method for improving glycemic control and/or for reducing of fasting plasma glucose, of postprandial plasma glucose and/or of glycosylated hemoglobin HbA1c in a patient in need thereof who is diagnosed with impaired glucose tolerance (IGT), impaired fasting blood glucose (IFG) with insulin resistance, with metabolic syndrome and/or with type 2 or type 1 diabetes mellitus characterized in that a pharmaceutical composition as defined hereinbefore and hereinafter is administered to the patient.

According to another preferred embodiment of the present invention, there is provided a method for improving gycemic control in patients, in particular in adult patients, with type 2 diabetes mellitus as an adjunct to diet and exercise.

Therefore, the method and/or use according to this invention is advantageously applicable in those patients who show one, two or more of the following conditions:
(a) insufficient glycemic control with diet and exercise alone;
(b) insufficient glycemic control despite oral monotherapy with metformin, in particular despite oral monotherapy at a maximal tolerated dose of metformin;
(c) insufficient glycemic control despite oral monotherapy with another antidiabetic agent, in particular despite oral monotherapy at a maximal tolerated dose of the other antidiabetic agent.

The lowering of the blood glucose level by the administration of a pharmaceutical composition according to this invention is insulin-independent. Therefore, a pharmaceutical composition according to this invention is particularly suitable in the treatment of patients who are diagnosed having one or more of the following conditions
insulin resistance,
hyperinsulinemia,
pre-diabetes,
type 2 diabetes mellitus, particular having a late stage type 2 diabetes mellitus,
type 1 diabetes mellitus.

Furthermore, a pharmaceutical composition according to this invention is particularly suitable in the treatment of patients who are diagnosed having one or more of the following conditions
(a) obesity (including class I, II and/or III obesity), visceral obesity and/or abdominal obesity,
(b) triglyceride blood level ≥150 mg/dL,
(c) HDL-cholesterol blood level <40 mg/dL in female patients and <50 mg/dL in male patients,
(d) a systolic blood pressure ≥130 mm Hg and a diastolic blood pressure ≥85 mm Hg,
(e) a fasting blood glucose level ≥110 mg/dL.

It is assumed that patients diagnosed with impaired glucose tolerance (IGT), impaired fasting blood glucose (IFG), with insulin resistance and/or with metabolic syndrome suffer from an increased risk of developing a cardiovascular disease, such as for example myocardial infarction, coronary heart disease, heart insufficiency, thromboembolic events. A glycemic control according to this invention may result in a reduction of the cardiovascular risks.

A pharmaceutical composition according to this invention exhibits a good safety profile. Therefore, a treatment or prophylaxis according to this invention is advantageously possible in those patients for which the mono-therapy with another antidiabetic drug is contraindicated and/or who have an intolerance against such drugs at therapeutic doses. In particular, a treatment or prophylaxis according to this invention may be advantageously possible in those patients showing or having an increased risk for one or more of the following disorders: renal insufficiency or diseases, cardiac diseases, cardiac failure, hepatic diseases, pulmonal diseases, catabolytic states and/or danger of lactate acidosis, or female patients being pregnant or during lactation.

Furthermore, it can be found that the administration of a pharmaceutical composition according to this invention results in no risk or in a low risk of hypoglycemia. Therefore, a treatment or prophylaxis according to this invention is also advantageously possible in those patients showing or having an increased risk for hypoglycemia.

A pharmaceutical composition according to this invention is particularly suitable in the long term treatment or prophylaxis of the diseases and/or conditions as described hereinbefore and hereinafter, in particular in the long term glycemic control in patients with type 2 diabetes mellitus.

The term "long term" as used hereinbefore and hereinafter indicates a treatment of or administration in a patient within a period of time longer than 12 weeks, preferably longer than 25 weeks, even more preferably longer than 1 year.

Therefore, a particularly preferred embodiment of the present invention provides a method for therapy, preferably oral therapy, for improvement, especially long term improvement, of glycemic control in patients with type 2 diabetes mellitus, especially in patients with late stage type 2 diabetes mellitus, in particular in patients additionally diagnosed of overweight, obesity (including class I, class II and/or class III obesity), visceral obesity and/or abdominal obesity.

According to another aspect of the invention, there is provided a method for preventing, slowing the progression of, delaying or treating of a condition or disorder selected from the group consisting of complications of diabetes mellitus such as cataracts and micro- and macrovascular diseases, such as dyslipidemia, nephropathy, retinopathy, neuropathy, tissue ischaemia, diabetic foot, arteriosclerosis, myocardial infarction, accute coronary syndrome, unstable angina pectoris, stable angina pectoris, stroke, peripheral arterial occlusive disease, cardiomyopathy, heart failure, heart rhythm disorders and vascular restenosis, in a patient in need thereof characterized in that a pharmaceutical composition according to the invention is administered to the patient. In particular one or more aspects of diabetic nephropathy such as hyperperfusion, proteinuria and albuminuria may be treated, their progression slowed or their onset delayed or prevented. The term "tissue ischaemia" particularly comprises diabetic macroangiopathy, diabetic microangiopathy, impaired wound healing and diabetic ulcer. The terms "micro- and macrovascular diseases" and "micro- and macrovascular complications" are used interchangeably in this application.

According to another aspect of the invention, there is provided a method for preventing, slowing the progression of, delaying or treating a metabolic disorder selected from the group consisting of type 2 diabetes mellitus, impaired glucose tolerance (IGT), impaired fasting blood glucose (IFG), hyperglycemia, postprandial hyperglycemia, overweight, obesity, metabolic syndrome, gestational diabetes and diabetes related to cystic fibrosis in a patient in need thereof characterized in that a pharmaceutical composition according to the invention is administered to the patient.

According to another aspect of the invention, there is provided a method for improving glycemic control and/or for reducing of fasting plasma glucose, of postprandial plasma glucose and/or of glycosylated hemoglobin HbA1c in a patient in need thereof characterized in that a pharmaceutical composition according to the invention is administered to the patient.

The pharmaceutical composition according to this invention may also have valuable disease-modifying properties with respect to diseases or conditions related to impaired glucose tolerance (IGT), impaired fasting blood glucose (IFG), insulin resistance and/or metabolic syndrome.

According to another aspect of the invention, there is provided a method for preventing, slowing, delaying or reversing progression from impaired glucose tolerance (IGT), impaired fasting blood glucose (IFG), insulin resistance and/or from metabolic syndrome to type 2 diabetes mellitus in a patient in need thereof characterized in that a pharmaceutical composition according to the invention is administered to the patient.

As by the use of a pharmaceutical composition according to this invention, an improvement of the glycemic control in patients in need thereof is obtainable, also those conditions and/or diseases related to or caused by an increased blood glucose level may be treated.

By the administration of a pharmaceutical composition according to this invention excessive blood glucose levels are not converted to insoluble storage forms, like fat, but excreted through the urine of the patient. It can be seen that loss of fat may account for the majority of the observed weight loss whereas no significant changes in body water or protein content are observed. Therefore, no gain in weight or even a reduction in body weight is the result.

According to another aspect of the invention, there is provided a method for reducing body weight and/or body fat or preventing an increase in body weight and/or body fat or facilitating a reduction in body weight and/or body fat in a patient in need thereof characterized in that a pharmaceutical composition according to the invention is administered to the patient.

By the administration of a combination or pharmaceutical composition according to the present invention, an abnormal accumulation of ectopic fat, in particular of the liver, may be reduced or inhibited. Therefore, according to another aspect of the present invention, there is provided a method for preventing, slowing, delaying or treating diseases or conditions attributed to an abnormal accumulation of ectopic fat, in particular of the liver, in a patient in need thereof characterized in that a pharmaceutical composition according to the invention is administered to the patient. Diseases or conditions which are attributed to an abnormal accumulation of liver fat are particularly selected from the group consisting of general fatty liver, non-alcoholic fatty liver (NAFL), non-alcoholic steatohepatitis (NASH), hyperalimentation-induced fatty liver, diabetic fatty liver, alcoholic-induced fatty liver or toxic fatty liver.

Another aspect of the invention provides a method for maintaining and/or improving the insulin sensitivity and/or for treating or preventing hyperinsulinemia and/or insulin resistance in a patient in need thereof characterized in that a pharmaceutical composition according to the invention is administered to the patient.

According to another aspect of the invention, there is provided a method for preventing, slowing progression of, delaying, or treating new onset diabetes after transplantation (NODAT) and/or post-transplant metabolic syndrome (PTMS) in a patient in need thereof characterized in that a pharmaceutical composition according to the invention is administered to the patient.

According to a further aspect of the invention, there is provided a method for preventing, delaying, or reducing NODAT and/or PTMS associated complications including micro- and macrovascular diseases and events, graft rejection, infection, and death in a patient in need thereof characterized in that a pharmaceutical composition according to the invention is administered to the patient.

The pharmaceutical composition according to the invention is capable of facilitating the lowering of serum total urate levels in the patient. Therefore according to another aspect of the invention, there is provided a method for treating hyperuricemia and hyperuricemia-associated conditions, such as for example gout, hypertension and renal failure, in a patient in need thereof characterized in that a pharmaceutical composition according to the invention is administered to the patient.

The administration of a pharmaceutical composition increases the urine excretion of glucose. This increase in osmotic excretion and water release and the lowering of urate levels are beneficial as a treatment or prevention for kidney stones. Therefore in a further aspect of the invention, there is provided a method for treating or preventing kidney stones in a patient in need thereof characterized in that a pharmaceutical composition according to the invention is administered to the patient.

The invention also relates to a pharmaceutical composition according to this invention for use in a method as described hereinbefore and hereinafter.

The invention also relates to a use of a pharmaceutical composition according to this invention for the manufacture of a medicament for use in a method as described hereinbefore and hereinafter.

DEFINITIONS

The term "active ingredient" of a pharmaceutical composition according to the present invention means the SGLT2 inhibitor, the DPP-4 inhibitor and/or metformin according to the present invention.

The term "body mass index" or "BMI" of a human patient is defined as the weight in kilograms divided by the square of the height in meters, such that BMI has units of $kg/m^2$.

The term "overweight" is defined as the condition wherein the individual has a BMI greater than or 25 $kg/m^2$ and less than 30 $kg/m^2$. The terms "overweight" and "pre-obese" are used interchangeably.

The term "obesity" is defined as the condition wherein the individual has a BMI equal to or greater than 30 $kg/m^2$. According to a WHO definition the term obesity may be categorized as follows: the term "class I obesity" is the condition wherein the BMI is equal to or greater than 30 $kg/m^2$ but lower than 35 $kg/m^2$; the term "class II obesity" is the condition wherein the BMI is equal to or greater than 35 $kg/m^2$ but lower than 40 $kg/m^2$; the term "class III obesity" is the condition wherein the BMI is equal to or greater than 40 $kg/m^2$.

The term "visceral obesity" is defined as the condition wherein a waist-to-hip ratio of greater than or equal to 1.0 in men and 0.8 in women is measured. It defines the risk for insulin resistance and the development of pre-diabetes.

The term "abdominal obesity" is usually defined as the condition wherein the waist circumference is >40 inches or 102 cm in men, and is >35 inches or 94 cm in women. With regard to a Japanese ethnicity or Japanese patients abdominal obesity may be defined as waist circumference ≥85 cm in men and ≥90 cm in women (see e.g. investigating committee for the diagnosis of metabolic syndrome in Japan).

The term "euglycemia" is defined as the condition in which a subject has a fasting blood glucose concentration within the normal range, greater than 70 mg/dL (3.89 mmol/L) and less than 100 mg/dL (5.6 mmol/L). The word "fasting" has the usual meaning as a medical term.

The term "hyperglycemia" is defined as the condition in which a subject has a fasting blood glucose concentration above the normal range, greater than 100 mg/dL (5.6 mmol/L). The word "fasting" has the usual meaning as a medical term.

The term "hypoglycemia" is defined as the condition in which a subject has a blood glucose concentration below the normal range, in particular below 70 mg/dL (3.89 mmol/L) or even below 60 mg/dl.

The term "postprandial hyperglycemia" is defined as the condition in which a subject has a 2 hour postprandial blood glucose or serum glucose concentration greater than 200 mg/dL (11.1 mmol/L).

The term "impaired fasting blood glucose" or "IFG" is defined as the condition in which a subject has a fasting blood glucose concentration or fasting serum glucose concentration in a range from 100 to 125 mg/dl (i.e. from 5.6 to 6.9 mmol/l), in particular greater than 110 mg/dL and less than 126 mg/dl (7.00 mmol/L). A subject with "normal fasting glucose" has a fasting glucose concentration smaller than 100 mg/dl, i.e. smaller than 5.6 mmol/l.

The term "impaired glucose tolerance" or "IGT" is defined as the condition in which a subject has a 2 hour postprandial blood glucose or serum glucose concentration greater than 140 mg/dl (7.8 mmol/L) and less than 200 mg/dL (11.11 mmol/L). The abnormal glucose tolerance, i.e. the 2 hour postprandial blood glucose or serum glucose concentration can be measured as the blood sugar level in mg of glucose per dL of plasma 2 hours after taking 75 g of glucose after a fast. A subject with "normal glucose tolerance" has a 2 hour postprandial blood glucose or serum glucose concentration smaller than 140 mg/dl (7.8 mmol/L).

The term "hyperinsulinemia" is defined as the condition in which a subject with insulin resistance, with or without euglycemia, has fasting or postprandial serum or plasma insulin concentration elevated above that of normal, lean individuals without insulin resistance, having a waist-to-hip ratio <1.0 (for men) or <0.8 (for women).

The terms "insulin-sensitizing", "insulin resistance-improving" or "insulin resistance-lowering" are synonymous and used interchangeably.

The term "insulin resistance" is defined as a state in which circulating insulin levels in excess of the normal response to a glucose load are required to maintain the euglycemic state (Ford ES, et al. *JAMA*. (2002) 287:356-9). A method of determining insulin resistance is the euglycaemic-hyperinsulinaemic clamp test. The ratio of insulin to glucose is determined within the scope of a combined insulin-glucose infusion technique. There is found to be insulin resistance if the glucose absorption is below the 25th percentile of the background population investigated (WHO definition). Rather less laborious than the clamp test are so called minimal models in which, during an intravenous glucose tolerance test, the insulin and glucose concentrations in the blood are measured at fixed time intervals and from these the insulin resistance is calculated. With this method, it is not possible to distinguish between hepatic and peripheral insulin resistance.

Furthermore, insulin resistance, the response of a patient with insulin resistance to therapy, insulin sensitivity and hyperinsulinemia may be quantified by assessing the "homeostasis model assessment to insulin resistance (HOMA-IR)" score, a reliable indicator of insulin resistance (Katsuki A, et al. Diabetes Care 2001; 24:362-5). Further reference is made to methods for the determination of the HOMA-index for insulin sensitivity (Matthews et al., *Diabetologia* 1985, 28:412-19), of the ratio of intact proinsulin to insulin (Forst et al., *Diabetes* 2003, 52(*Suppl.* 1): A459) and to an euglycemic clamp study. In addition, plasma adiponectin levels can be monitored as a potential surrogate of insulin sensitivity. The estimate of insulin resistance by the homeostasis assessment model (HOMA)-IR score is calculated with the formula (Galvin P, et al. Diabet Med 1992;9:921-8):

$$\text{HOMA-IR} = [\text{fasting serum insulin } (\mu U/mL)] \times [\text{fasting plasma glucose(mmol/L)}/22.5]$$

As a rule, other parameters are used in everyday clinical practice to assess insulin resistance. Preferably, the patient's triglyceride concentration is used, for example, as increased triglyceride levels correlate significantly with the presence of insulin resistance.

Patients with a predisposition for the development of IGT or IFG or type 2 diabetes are those having euglycemia with hyperinsulinemia and are by definition, insulin resistant. A typical patient with insulin resistance is usually overweight or obese, but this is not always the case. If insulin resistance can be detected, this is a particularly strong indication of the presence of pre-diabetes. Thus, it may be that in order to maintain glucose homoeostasis a person have e.g. 2-3 times as high endogenous insulin production as a healthy person, without this resulting in any clinical symptoms.

The methods to investigate the function of pancreatic beta-cells are similar to the above methods with regard to insulin sensitivity, hyperinsulinemia or insulin resistance: An improvement of beta-cell function can be measured for example by determining a HOMA-index for beta-cell function (Matthews et al., *Diabetologia* 1985, 28:412-19), the ratio of intact proinsulin to insulin (Forst et al., *Diabetes* 2003, 52(*Suppl.* 1): A459), the insulin/C-peptide secretion after an oral glucose tolerance test or a meal tolerance test, or by employing a hyperglycemic clamp study and/or minimal modeling after a frequently sampled intravenous glucose tolerance test (Stumvoll et al., *Eur J Clin Invest* 2001, 31:380-81).

The term "pre-diabetes" is the condition wherein an individual is pre-disposed to the development of type 2 diabetes. Pre-diabetes extends the definition of impaired glucose tolerance to include individuals with a fasting blood glucose within the high normal range ≥100 mg/dL (J. B. Meigs, et al. Diabetes 2003; 52:1475-1484) and fasting hyperinsulinemia (elevated plasma insulin concentration). The scientific and medical basis for identifying pre-diabetes as a serious health threat is laid out in a Position Statement entitled "The Prevention or Delay of Type 2 Diabetes" issued jointly by the American Diabetes Association and the National Institute of Diabetes and Digestive and Kidney Diseases (Diabetes Care 2002; 25:742-749).

Individuals likely to have insulin resistance are those who have two or more of the following attributes: 1) overweight or obese, 2) high blood pressure, 3) hyperlipidemia, 4) one or more 1$^{st}$ degree relative with a diagnosis of IGT or IFG or type 2 diabetes. Insulin resistance can be confirmed in these individuals by calculating the HOMA-IR score. For the purpose of this invention, insulin resistance is defined as the clinical condition in which an individual has a HOMA-IR score >4.0 or a HOMA-IR score above the upper limit of normal as defined for the laboratory performing the glucose and insulin assays.

The term "type 1 diabetes" is defined as the condition in which a subject has, in the presence of autoimmunity towards the pancreatic beta-cell or insulin, a fasting blood glucose or serum glucose concentration greater than 125 mg/dL (6.94 mmol/L). If a glucose tolerance test is carried out, the blood sugar level of a diabetic will be in excess of 200 mg of glucose per dL (11.1 mmol/l) of plasma 2 hours after 75 g of glucose have been taken on an empty stomach, in the presence of autoimmunity towards the pancreatic beta cell or insulin. In a glucose tolerance test 75 g of glucose are administered orally to the patient being tested after 10-12 hours of fasting and the blood sugar level is recorded immediately before taking the glucose and 1 and 2 hours after taking it. The presence of autoimmunity towards the pancreatic beta-cell may be observed by detection of circulating islet cell autoantibodies ["type 1A diabetes mellitus"], i.e., at least one of: GAD65 [glutamic acid decarboxylase-65], ICA [islet-cell cytoplasm], IA-2 [intracytoplasmic domain of the tyrosine phosphatase-like protein IA-2], ZnT8 [zinc-transporter-8] or anti-insulin; or other signs of autoimmunity without the presence of typical circulating autoantibodies [type 1B diabetes], i.e. as detected through pancreatic biopsy or imaging). Typically a genetic predisposition is present (e.g. HLA, INS VNTR and PTPN22), but this is not always the case.

The term "type 2 diabetes" is defined as the condition in which a subject has a fasting blood glucose or serum glucose concentration greater than 125 mg/dL (6.94 mmol/L). The measurement of blood glucose values is a standard procedure in routine medical analysis. If a glucose tolerance test is carried out, the blood sugar level of a diabetic will be in excess of 200 mg of glucose per dL (11.1 mmol/l) of plasma 2 hours after 75 g of glucose have been taken on an empty stomach. In a glucose tolerance test 75 g of glucose are administered orally to the patient being tested after 10-12 hours of fasting and the blood sugar level is recorded immediately before taking the glucose and 1 and 2 hours after taking it. In a healthy subject, the blood sugar level before taking the glucose will be between 60 and 110 mg per dL of plasma, less than 200 mg per dL 1 hour after taking the glucose and less than 140 mg per dL after 2 hours. If after 2 hours the value is between 140 and 200 mg, this is regarded as abnormal glucose tolerance.

The term "late stage type 2 diabetes mellitus" includes patients with a secondary drug failure, indication for insulin therapy and progression to micro- and macrovascular complications e.g. diabetic nephropathy, or coronary heart disease (CHD).

The term "HbA1c" refers to the product of a non-enzymatic glycation of the haemoglobin B chain. Its determination is well known to one skilled in the art. In monitoring the treatment of diabetes mellitus the HbA1c value is of exceptional importance. As its production depends essentially on the blood sugar level and the life of the erythrocytes, the HbA1c in the sense of a "blood sugar memory" reflects the average blood sugar levels of the preceding 4-6 weeks. Diabetic patients whose HbA1c value is consistently well adjusted by intensive diabetes treatment (i.e. <6.5% of the total haemoglobin in the sample), are significantly better protected against diabetic microangiopathy. For example, metformin on its own achieves an average improvement in the HbA1c value in the diabetic of the order of 1.0-1.5%. This reduction of the HbA1C value is not sufficient in all diabetics to achieve the desired target range of <6.5% and preferably <6% HbA1c.

The term "insufficient glycemic control" or "inadequate glycemic control" in the scope of the present invention means a condition wherein patients show HbA1c values above 6.5%, in particular above 7.0%, even more preferably above 7.5%, especially above 8%.

The "metabolic syndrome", also called "syndrome X" (when used in the context of a metabolic disorder), also called the "dysmetabolic syndrome" is a syndrome complex with the cardinal feature being insulin resistance (Laaksonen DE, et al. *Am J Epidemiol* 2002; 156:1070-7). According to the ATP III/NCEP guidelines (Executive Summary of the Third Report of the National Cholesterol Education Program (NCEP) Expert Panel on Detection, Evaluation, and Treatment of High Blood Cholesterol in Adults (Adult Treatment Panel III) *JAMA: Journal of the American Medical Association* (2001) 285:2486-2497), diagnosis of the metabolic syndrome is made when three or more of the following risk factors are present:

1. Abdominal obesity, defined as waist circumference >40 inches or 102 cm in men, and >35 inches or 94 cm in women; or with regard to a Japanese ethnicity or Japanese patients defined as waist circumference ≥85 cm in men and ≥90 cm in women;
2. Triglycerides: ≥150 mg/dL
3. HDL-cholesterol <40 mg/dL in men
4. Blood pressure ≥130/85 mm Hg (SBP ≥130 or DBP ≥85)
5. Fasting blood glucose ≥100 mg/dL The NCEP definitions have been validated (Laaksonen DE, et al. *Am J Epidemiol.* (2002) 156:1070-7). Triglycerides and HDL cholesterol in the blood can also be determined by standard methods in medical analysis and are described for example in Thomas L (Editor): "Labor and Diagnose", TH-Books Verlagsgesellschaft mbH, Frankfurt/Main, 2000.

According to a commonly used definition, hypertension is diagnosed if the systolic blood pressure (SBP) exceeds a value of 140 mm Hg and diastolic blood pressure (DBP) exceeds a value of 90 mm Hg. If a patient is suffering from manifest diabetes it is currently recommended that the systolic blood pressure be reduced to a level below 130 mm Hg and the diastolic blood pressure be lowered to below 80 mm Hg.

The definitions of NODAT (new onset diabetes after transplantation) and PTMS (post-transplant metabolic syndrome) follow closely that of the American Diabetes Association diagnostic criteria for type 2 diabetes, and that of the International Diabetes Federation (IDF) and the American Heart Association/National Heart, Lung, and Blood Institute, for the metabolic syndrome. NODAT and/or PTMS are associated with an increased risk of micro- and macrovascular disease and events, graft rejection, infection, and death. A number of predictors have been identified as potential risk factors related to NODAT and/or PTMS including a higher age at transplant, male gender, the pre-transplant body mass index, pre-transplant diabetes, and immunosuppression.

The term "gestational diabetes" (diabetes of pregnancy) denotes a form of the diabetes which develops during pregnancy and usually ceases again immediately after the birth. Gestational diabetes is diagnosed by a screening test which is carried out between the 24th and 28th weeks of pregnancy. It is usually a simple test in which the blood sugar level is measured one hour after the administration of 50 g of glucose solution. If this 1 h level is above 140 mg/dl, gestational diabetes is suspected. Final confirmation may be obtained by a standard glucose tolerance test, for example with 75 g of glucose.

The term "hyperuricemia" denotes a condition of high serum total urate levels. In human blood, uric acid concentrations between 3.6 mg/dL (ca. 214 µmol/L) and 8.3 mg/dL (ca. 494 µmol/L) are considered normal by the American Medical Association. High serum total urate levels, or hyperuricemia, are often associated with several maladies. For example, high serum total urate levels can lead to a type of arthritis in the joints known as gout. Gout is a condition created by a build up of monosodium urate or uric acid crystals on the articular cartilage of joints, tendons and surrounding tissues due to elevated concentrations of total urate levels in the blood stream. The build up of urate or uric acid on these tissues provokes an inflammatory reaction of these tissues. Saturation levels of uric acid in urine may result in kidney stone formation when the uric acid or urate crystallizes in the kidney. Additionally, high serum total urate levels are often associated with the so-called metabolic syndrome, including cardiovascular disease and hypertension.

The term "hyponatremia" denotes a condition of a positive balance of water with or without a deficit of sodium, which is recognized when the plasma sodium falls below the level of 135 mml/L. Hyponatremia is a condition which can occur in isolation in individuals that over-consume water; however, more often hyponatremia is a complication of medication or other underlying medical condition that leas to a diminished excretion of water. Hyponatremia may lead to water intoxication, which occurs when the normal tonicity of extracellular fluid falls below the safe limit, due to retention of excess water. Water intoxication is a potentially fatal disturbance in brain function. Typical symptoms of water intoxication include nausea, vomiting, headache and malaise.

The terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy.

The terms "prophylactically treating", "preventivally treating" and "preventing" are used interchangeably and comprise a treatment of patients at risk to develop a condition mentioned hereinbefore, thus reducing said risk.

The invention claimed is:

1. A pharmaceutical composition comprising:
  a) an inner extended release core, wherein the inner extended release core is a formulation comprising metformin hydrochloride, a swellable and/or extended release polymer, and one or more further excipients;
  b) an intermediate seal coating; and
  c) an outer immediate release coating, wherein the outer immediate release coating is a film coat formulation comprising the SGLT2-inhibitor 1-chloro-4-(β-D-glucopyranos-1-yl)-2-[4-((S)-tetrahydrofuran-3-yloxy)-benzyl]-benzene, a film-coating agent, a plasticizer, and, optionally, a glidant.

2. The pharmaceutical composition according to claim 1, wherein the film-coating agent is hydroxypropyl methylcellulose.

3. The pharmaceutical composition according to claim 1, wherein the plasticizer is polyethylene glycol.

4. The pharmaceutical composition according to claim 1, wherein the plasticizer is propylene glycol.

5. The pharmaceutical composition according to claim 1, wherein the optional glidant is talc.

6. The pharmaceutical composition according to claim 1, wherein the seal coating comprises a film-coating agent, a plasticizer, and, optionally, a glidant, one or more pigments and/or colors.

7. The pharmaceutical composition according to claim 1, wherein the metformin hydrochloride is present in a unit dosage strength of 500, 750, 850, 1000 or 1500 mg.

8. The pharmaceutical composition according to claim 1, wherein the SGLT-2 inhibitor is present in a unit dosage strength of 5, 10, 12.5 or 25 mg.

9. The pharmaceutical composition according to claim 1, which is a tablet for oral administration.

10. The tablet according to claim 9 further comprising an outer film over-coat.

11. The tablet according to claim 10, wherein the outer film over-coat comprises a film-coating agent, a plasticizer, and, optionally, a glidant, one or more pigments and/or colors.

12. A method of using the pharmaceutical composition according to claim 1 for treating, preventing, slowing the progression, or delaying the onset of metabolic diseases either in type 2 diabetes patients who have not been previously treated with an antihyperglycemic agent, or
  in type 2 diabetes patients with insufficient glycemic control despite therapy with one or two conventional antihyperglycemic agents selected from metformin, sulphonylureas, thiazolidinediones, glinides, alpha-glucosidase blockers, GLP-1 or GLP-1 analogues, and insulin or insulin analogues; comprising administering the composition of claim 1 to said patient.

13. The method of claim 12, wherein the metabolic disease is type 2 diabetes mellitus and conditions related thereto.

14. The pharmaceutical composition according to claim 2, wherein the hydroxypropyl methylcellulose is Hypromellose 2910, Methocel E5, or Methocel E15.

15. The pharmaceutical composition according to claim 3, wherein the polyethylene glycol is Macrogol 400, 6000 or 8000.

16. The pharmaceutical composition according to claim 1, wherein the dosage strength is 5 mg of the SGLT2 inhibitor and 1000 mg metformin hydrochloride.

17. The pharmaceutical composition according to claim 1, wherein the dosage strength is 10 mg of the SGLT2 inhibitor and 1000 mg metformin hydrochloride.

18. The pharmaceutical composition according to claim 1, wherein the dosage strength is 12.5 mg of the SGLT2 inhibitor and 1000 mg metformin hydrochloride.

19. The pharmaceutical composition according to claim 1, wherein the dosage strength is 25 mg of the SGLT2 inhibitor and 1000 mg metformin hydrochloride.

20. The pharmaceutical composition according to claim 1, wherein the extended release material comprises poly(ethylene oxide) and/or hydroxypropyl methylcellulose (HPMC).

21. The pharmaceutical composition according to claim 6, wherein the film coating agent is a mixture of hydroxypropylcellulose and hydroxypropyl methylcellulose.

22. The pharmaceutical composition according to claim 1, wherein the outer immediate release coating comprises the SGLT2 inhibitor and 1-[(4-methyl-quinazolin-2- yl)methyl]-3-methyl-7-(2-butyn-1-yl)-8-(3-(R)-amino-piperidin-1-yl)-xanthine.

* * * * *